US006651015B2

(12) United States Patent
Samsoondar

(10) Patent No.: US 6,651,015 B2
(45) Date of Patent: *Nov. 18, 2003

(54) METHOD FOR CALIBRATING SPECTROPHOTOMETRIC APPARATUS

(76) Inventor: James Samsoondar, 40 Hilborn Avenue, Cambridge, Ontario (CA), N1T 1M7

( * ) Notice: Subject to any disclaimer, the term of this patent is extended or adjusted under 35 U.S.C. 154(b) by 0 days.

This patent is subject to a terminal disclaimer.

(21) Appl. No.: 10/259,838

(22) Filed: Sep. 30, 2002

(65) Prior Publication Data

US 2003/0093230 A1 May 15, 2003

Related U.S. Application Data

(63) Continuation-in-part of application No. 10/200,594, filed on Jul. 23, 2002, which is a continuation-in-part of application No. 10/187,437, filed on Jul. 2, 2002, which is a continuation-in-part of application No. 09/875,227, filed on Jun. 7, 2001, which is a continuation-in-part of application No. 09/773,495, filed on Feb. 2, 2001, now abandoned, which is a continuation-in-part of application No. 09/697,679, filed on Oct. 27, 2000, now abandoned, which is a continuation-in-part of application No. 09/447,215, filed on Nov. 23, 1999, now Pat. No. 6,470,279.

(51) Int. Cl.[7] .......................... G01R 13/00; G06F 19/00
(52) U.S. Cl. ........................................... 702/66; 702/28
(58) Field of Search ...................... 702/28, 66

(56) References Cited

U.S. PATENT DOCUMENTS 4,866,644 A 9/1989 Shenk et al. ............ 364/571.02

FOREIGN PATENT DOCUMENTS

| WO | WO 94/08225 | 4/1994 | .......... G01N/21/27 |
|----|-------------|--------|----------------------|
| WO | WO 97/47972 | 12/1997 | .......... G01N/33/96 |
| WO | WO 98/38961 | 9/1998 | ............. A61J/1/00 |
| WO | WO 98/39634 | 9/1998 | .......... G01N/21/27 |

OTHER PUBLICATIONS

Martinek, Robert G., "Liquid Absorbance Standards for Ultraviolet, Visible, and Near Infrared Spectrophotometry" *J. Amer. Med. Technol.*, Vol. 40 (1978) pp. 210–216.

Ozdemir, et al., "Hybrid Calibration Models: An Alternative to Calibration Transfer" *Applied Spectroscopy*, Vol. 52, No. 4 (1998) pp 599–603.

Bouveresse, et al., "Calibration transfer across near–infrared spectrometric instruments using Shenk's algorithm: effects of different standarisation samples" *Analytica Chimica Acta*, Vol. 297 (1994) pp. 405–416.

Blank, et al., "Transfer of Near–Infrared Multivariate Calibrations without Standards" *Analytical Chemistry*, Vol. 68, No. 17 (1996) pp. 2987–2995.

Blanco, et al., "Wavelength Calibration Transfer between Diode Array UV–Visible Spectrophotometers" *Applied Spectroscopy*, Vol. 49, No. 5 (1995) pp. 593–597.

Wang, et al., "Multivariate Instrument Standardization" *Analytical Chemistry*, Vol. 63, no. 23 (1991) pp. 2750–2756.

Gemperline, et al., "Appearance of Discontinuities in Spectra Transformed by the Piecewise Direct Instrument Standardization Procedure" *Analytical Chemistry*, Vol. 68, No. 17 (1996) pp. 2913–2915.

*Primary Examiner*—John Barlow
*Assistant Examiner*—Aditya Bhat
(74) *Attorney, Agent, or Firm*—Katten Muchin Zavis Rosenman

(57) ABSTRACT

Described is a method for determining the concentration of an analyte in a future sample that is measured on a second apparatus. This method involves incorporating, in a second apparatus, at least one primary calibration algorithm that is developed using absorbances of samples from a primary calibration set. The absorbances, which are optionally preprocessed prior to primary calibration algorithm development, are obtained from one or more first apparatus. The absorbance values of the future sample are measured on the second apparatus at one or more than one wavelength from a standard set of wavelengths, and a concentration of the analyte in the future sample is calculated by applying the Primary Calibration Algorithm to the optionally preprocessed absorbance of the future sample obtained from the second apparatus.

83 Claims, 19 Drawing Sheets

METHOD FOR CALIBRATING SPECTROPHOTOMETRIC APPARATUS

This is a Continuation-In-Part Application of a U.S. application Ser. No. 10/200,594, filed Jul. 23, 2002, which is a Continuation-in-Part Application of U.S. application Ser. No. 10/187,437, filed Jul. 2, 2002, which is a Continuation-in-Part Application of U.S. application Ser. No. 09/875,227 filed Jun. 7, 2001, which is a continuation-in-part of a U.S. application Ser. No. 09/773,495 filed Feb. 2, 2001 now abandoned, which is a continuation-in-part of a U.S. application Ser. No. 09/697,679 filed Oct. 27, 2000 now abandoned, which is a continuation-in-part of U.S. application Ser. No. 09/447,215 filed Nov. 23, 1999 now U.S. Pat. No. 6,470,279.

FIELD OF INVENTION

This invention is in the field of spectrophotometric determinations of concentrations of analytes in samples. The invention further relates to methods of calibrating spectrophotometers. Particularly, the method relates to the calibration of spectrophotometric apparatus designed to measure interferents in serum and plasma.

BACKGROUND OF INVENTION

Clinical laboratory tests are routinely performed on serum or plasma of whole blood. In a routine assay, red blood cells are separated from plasma by centrifugation. Red blood cells and various plasma proteins may also be separated from serum by clotting prior to centrifugation. Hemoglobin (Hb), light-scattering substances like lipid particles, bile pigments bilirubin (BR) and biliverdin (BV) are typical substances which will interfere with and affect spectrophotometric and other blood analytical measurements and are therefore referred to as interferents. The presence of such interferents affects the ability to perform tests on the serum or plasma and as such can be the to compromise specimen integrity.

Visual inspection can be used to determine the presence of interferents in serum and plasma but such a method relies on the experience and knowledge of the observer and is therefore unreliable. The use of an apparatus or instrument to measure interferents in serum and plasma i.e., assess specimen integrity, is a substitute for visual inspection and the interferents may be regarded as analytes with respect to the apparatus. Measurement of interferents is taught in WO 9838961 and WO 9839634. Because quantitative results from the determination of the concentration of such interferents are reported based on specific calibration algorithms, there is a need to calibrate and to monitor calibration performance daily.

Unlike many blood analytical apparatus, calibration of reagentless spectrophotometric apparatus used to measure the concentration of analytes or interferents in a serum or plasma sample is a cumbersome time intensive exercise. Each apparatus used for the purposes of determining the concentration of interferents must be calibrated according to procedures known in the art, for example, the process described herein, in the section titled "Primary Calibration," and over the lifetime of an apparatus can amount to a considerable amount of time and cost. Furthermore, in settings where a large number of apparatus is needed to perform multiple sample measurements (such as blood banks for example) the time required for calibration can become a real burden on the efficiency of the of the quality control process.

Martinek (J. Amer. Med. Technol., July–August 1978, p. 210–216) teaches a method of photometric correction, involving liquid absorbance standards to correct one spectrophotometer to match another using a slope and bias correction. This method may also be used for test methods that require reagents.

U.S. Pat. No. 4,866,644 teaches a method of calibrating a second apparatus to produce results for a test sample, as if the sample was tested on a first apparatus. The method combines photometric correction with a mathematical process that computes a waveshift for each index point. The waveshifts are derived from the assessment of readings determined for a plurality of samples on the two apparatus. The waveshifts are applied as corrections to an existing wavelength calibration table of the second apparatus in order to make the second apparatus behave in a manner similar to the first apparatus. In U.S. Pat. No. 4,866,644, the same wavelengths are assigned to the same corresponding index points in every instrument. Therefore, there is no derivation of a new wavelength calibration table of the second instrument, and the waveshift correction is applied to each measurement as it is determined on the second instrument.

Ozdemir, D et al (Applied Spectroscopy, Volume 52 No. 4, 1998, p599–603) described an alternative to calibration transfer, referred to as "Hybrid Calibration Models," which teaches the inclusion of calibration data obtained from more than one instruments, in developing primary calibration algorithms.

WO 94/08225 discloses a method involving the modification of the constants of a primary calibration algorithm of a second or recalibrated apparatus, to yield results consistent with a first apparatus that is in control. A limitation of this method is that the number of samples required must be at least one more than the number of terms used in the primary calibration equation, because a mathematical system of "simultaneous equations" is used to generate a new constant for each term in the primary calibration algorithm. Furthermore, a predicted dependant variable, such as a chemical or physical property, of a calibrator is required to generate the new constants.

WO 97/47942 teaches a method for a second apparatus to produce results for a test sample, as if the sample was tested on the first apparatus involving testing a set of stable samples, whose absorbance spectra mimic that of the analytes, on both the first and a second apparatus, and predicting the analyte concentrations after applying a primary calibration algorithm. This method requires a predicted dependant variable, for example a chemical or physical property, of the calibrator. Analyte results predicted by both apparatus are used to perform a slope and bias correction of each analyte prediction on a test sample. The calibration set requires the property of having an absorbance spectra similar to the analyte.

There is a need for a method to simply and accurately calibrate a second apparatus, and to recalibrate a first or second apparatus that is no longer in control.

It is an object of the invention to overcome disadvantages of the prior art.

The above object is met by the combinations of features of the main claims, the sub-claims disclose further advantageous embodiments of the invention.

SUMMARY OF INVENTION

This invention is in the field of spectrophotometric determination of concentrations of analytes in samples. The invention further relates to methods of calibrating spectrophotometers. The method may be used for the calibration of spectrophotometric apparatus designed to measure interferents in serum and plasma. The invention also relates to a method of transferring calibration algorithms from a first apparatus to a second apparatus, with the optional use of data pre-processing techniques, and photometric correction.

The present inventor has found that for a given analyte, a "Primary Calibration Algorithm" developed for a "First apparatus" can be transferred onto a "Second Apparatus". Therefore, the Second Apparatus need not be subjected to the cumbersome, time intensive Primary Calibration process.

In one aspect of the invention, the First Apparatus that is known to be "in Control" is used to assign absorbance values to a "Set of Calibrators" from a batch or lot, and any Second Apparatus can be calibrated rapidly by a process of "Calibration Algorithm Transfer," and the concentration of an analyte in a sample determined by applying the "Primary Calibration Algorithm" to a corrected interpolated absorbance measurement of the sample. Therefore, the present invention provides a method for calibrating a Second Apparatus using a Set of Calibrators with absorbances assigned by the First Apparatus.

In yet a further aspect of the invention a method for adjusting the absorbance of sample obtained on a second apparatus to normalize it with that of a first apparatus that is in control ("photometric correction") using a "Linear Regression Equation" is also provided.

The present invention provides a method (A) of determining the concentration of one or more Analytes in a Sample in a second apparatus comprising:
  (i) incorporating at least one primary calibration algorithm that uses an order derivative of absorbance obtained for at least one of a standard set of wavelengths, on the second apparatus;
  (ii) measuring absorbance values of the sample at one or more than one wavelength from the standard set of wavelengths on the second apparatus;
  (iii) obtaining the order derivative of the absorbance values;
    a) if the order derivative is not zero, then using the order derivative and calculating a concentration of the Analyte in the sample, by applying the Primary Calibration Algorithm to the order derivative of absorbance obtained;
    b) if the order derivative is zero, then calculating a concentration of the Analyte in the sample, by applying the Primary Calibration Algorithm to the absorbance values.

The present invention pertains to the method (A) defined above, wherein in the step of incorporating (step (i)), and in the step of obtaining (step (iii)), the order derivative, is of a zero, first, second, or third order. Furthermore, a statistical technique selected from the group consisting of simple linear regression, multiple linear regression, and Multivariate data analysis, may be used to process absorbance measurements for the development of the at least one primary calibration algorithm, the Multivariate data analysis selected from the group consisting of Principal Component Analysis, Principal Component Regression, Partial Least Squares regression, and Neural Network. Also, the present invention provides a step of data pre-processing following the step of measuring (step ii)), wherein data pre-processing is selected from the group consisting of calculation of interpolated absorbances; smoothing of absorbances; calculation of a first and higher order derivative of absorbance; multiplicative scatter correction; data transformation; photometric correction, and any combination thereof.

The present invention provides the method (A), above, wherein the second apparatus comprises a second linear diode array comprising the same number of pixels as a first linear diode array in a first apparatus.

The present invention embraces the method (A) above, wherein in the step of incorporating (step (i)), and wherein in the step of measuring (step (ii)), the standard set of wavelengths is a set of approximate wavelengths derived from a wavelength calibration table of a first apparatus, the second apparatus, or both a first and the second apparatus.

The present invention pertains to the method (A) above, wherein in the step of incorporating (step (i)), and wherein in the step of measuring (step (ii)), the standard set of wavelengths comprises wavelengths that are common to a wavelength calibration table of both a first apparatus used to obtain the primary calibration algorithm, and the second apparatus.

This invention also includes the method (A) above, wherein in the step of incorporating (step (i)), the at least one primary calibration algorithm is developed from a combination of measurements obtained from one or more primary calibrators measured on a first apparatus and one or more similar apparatus.

The present invention also pertains to the method (A), above, wherein the standard set of wavelengths comprises wavelengths from about 300 nm to about 2500 nm, or wherein the standard set of wavelengths comprises wavelengths from about 500 nm to about 1100 nm.

The present invention embraces the method (A) above, wherein, in the step of measuring (step ii)), Photometric Correction is performed.

The present invention also provides the method (A) above, wherein in the steps of incorporating (step (i)), and measuring (step (ii)), the standard set of wavelengths is obtained by creating a table of approximate wavelengths derived from a first, a second or both the first and the second wavelength calibration table, wherein a pixel number of a linear diode array of the first apparatus and a pixel number of a second linear diode array of the second apparatus must be within less than or equal to about ±N pixel of a reference pixel number of the first apparatus, where, N is a number of pixels that encompass a range of wavelengths of no more than about ±20 nm, wherein the reference pixel number of the first apparatus is associated with a known wavelength of electromagnetic radiation.

The present invention embraces the method (A), above, wherein the wavelength calibration table for the first apparatus or the second apparatus is obtained by:
  (i) projecting a first electromagnetic radiation of known wavelength, onto a first pixel of a first linear diode array of the first apparatus, or a second linear diode array of the second apparatus;
  (ii) using a second electromagnetic radiation of known wavelength, the second electromagnetic radiation having a different wavelength than the first electromagnetic radiation, projecting the second electromagnetic radiation onto a second pixel of the first or the second linear diode array;
  (iii) identifying the first and second pixels within the first or the second linear diode array;
  (iv) calculating a pixeldispersion for the first or the second linear diode array; and
  (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

Also included within the present invention is the method (A), above, wherein the wavelength calibration table for the first or the second apparatus is obtained by:
(a) projecting a known wavelength of electromagnetic radiation, onto a pixel in a linear diode array of the first apparatus, or the second apparatus;
(b) identifying pixel number of the pixel;
(c) assigning a wavelength to each pixel within the linear diode array to produce the first, second, or both the first and the second wavelength calibration table using a predetermined pixeldispersion, the known wavelength of electromagnetic radiation and the pixel number.

The present invention also provides a method (B) of determining the concentration of one or more Analytes in a Sample in a second apparatus comprising:
(i) incorporating at least one primary calibration algorithm that uses an order derivative of absorbance obtained for at least one of a standard set of wavelengths, on the second apparatus, where wavelengths of the standard set of wavelengths are the same as wavelengths of a wavelength calibration table on the second apparatus;
(ii) measuring absorbance values of the sample at one or more wavelengths from the standard set of wavelengths, on the second apparatus;
(iii) obtaining the order derivative of the absorbance values;
   a) if the order derivative is not zero, then using the order derivative and calculating a concentration of the Analyte in the sample, by applying the Primary Calibration Algorithm to the order derivative of absorbance obtained;
   b) if the order derivative is zero, then calculating a concentration of the Analyte in the sample, by applying the Primary Calibration Algorithm to the absorbance values.

This invention embraces the method (B) above, wherein in the step of incorporating (step (i)), the at least one primary calibration algorithm is developed from a combination of measurements obtained from one or more primary calibrators measured on a first apparatus and one or more similar apparatus.

The present invention also includes the method (B), wherein in the step of incorporating (step (i)), and in the step of obtaining (step (iii)), the order derivative, is of a zero, first, second, or third order.

The present invention also pertains to the method (B), above, wherein a statistical technique selected from the group consisting of simple linear regression, multiple linear regression, and Multivariate data analysis, is used to process absorbance measurements for the development of the at least one primary calibration algorithm, and wherein the Multivariate data analysis is selected from the group consisting of Principal Component Analysis, Principal Component Regression, Partial Least Squares regression, and Neural Network. Furthermore, a step of data pre-processing may follow the step of measuring (step ii)) of Method (B), wherein data preprocessing is selected from the group consisting of calculation of interpolated absorbances; smoothing of absorbances; calculation of a first and higher order derivative of absorbance; multiplicative scatter correction; data transformation; photometric correction, and any combination thereof.

The present invention embraces the method (B) above, wherein, in the step of measuring (step ii)), Photometric Correction is performed.

The present invention also pertains to the method (B), above, wherein in the steps of incorporating (step (i)), and measuring (step (ii)), the standard set of wavelengths is obtained by creating a table of approximate wavelengths derived from a first, a second or both the first and the second wavelength calibration table, wherein a pixel number of a linear diode array of the first apparatus and a pixel number of a second linear diode array of the second apparatus must be within less than or equal to about ±N pixel of a reference pixel number of the first apparatus, where, N is a number of pixels that encompass a range of wavelengths of no more than about ±20 nm, wherein the reference pixel number of the first apparatus is associated with a known wavelength of electromagnetic radiation.

The present invention provides the method (B), above, wherein the wavelength calibration table for the first apparatus or the second apparatus is obtained by:
(i) projecting a first electromagnetic radiation of known wavelength, onto a first pixel of a first linear diode array of the first apparatus, or a second linear diode array of the second apparatus;
(ii) using a second electromagnetic radiation of known wavelength, the second electromagnetic radiation having a different wavelength than the first electromagnetic radiation, projecting the second electromagnetic radiation onto a second pixel of the first or the second linear diode array;
(iii) identifying the first and second pixels within the first or the second linear diode array;
(iv) calculating a pixeldispersion for the first or the second linear diode array; and
(v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

The present invention also pertains to the method (B), above, wherein the wavelength calibration table for the first or the second apparatus is obtained by:
(a) projecting a known wavelength of electromagnetic radiation, onto a pixel in a linear diode array of the first apparatus, or the second apparatus;
(b) identifying pixel number of the pixel;
(c) assigning a wavelength to each pixel within the linear diode array to produce the first, second, or both the first and the second wavelength calibration table using a predetermined pixeldispersion, the known wavelength of electromagnetic radiation and the pixel number.

The present invention also provides a method (C), of determining the concentration of at least one Analyte in a Sample in a second apparatus comprising:
(i) incorporating at least one upgraded primary calibration algorithm on the second apparatus, the at least one upgraded primary calibration algorithm developed by combining an original primary calibration data set obtained from one or more first apparatus for at least one of a standard set of wavelengths, with additional data from the second apparatus, the additional data obtained using a smaller similar primary calibration set, a subset primary calibration set, or both, for at least one of a standard set of wavelengths;
(ii) measuring absorbance values of the sample at one or more wavelengths from the standard set of wavelengths, on the second apparatus;

(iii) obtaining the order derivative of the absorbance values;
    a) if the order derivative is not zero, then using the order derivative and calculating a concentration of the Analyte in the sample, by applying the Primary Calibration Algorithm to the order derivative obtained;
    b) if the order derivative is zero, then calculating a concentration of the Analyte in the sample, by applying the Primary Calibration Algorithm to the absorbance values.

The present invention embraces the method (C), above, wherein in the step of incorporating (step (i)), and in the step of obtaining (step (iii)), the order derivative, is of a zero, first, second, or third order.

The present invention also pertains to the method (C), above, wherein a statistical technique selected from the group consisting of simple linear regression, multiple linear regression, and Multivariate data analysis, is used to process absorbance measurements for the development of the at least one primary calibration algorithm, and wherein the Multivariate data analysis is selected from the group consisting of Principal Component Analysis, Principal Component Regression, Partial Least Squares regression, and Neural Network. Furthermore, a step of data pre-processing may follow the step of measuring (step ii)) of Method (B), wherein data preprocessing is selected from the group consisting of calculation of interpolated absorbances; smoothing of absorbances; calculation of a first and higher order derivative of absorbance; multiplicative scatter correction; data transformation; photometric correction, and any combination thereof.

The present invention embraces the method (C) above, wherein, in the step of measuring (step ii)), Photometric Correction is performed.

The present invention also pertains to the method (C), above, wherein in the steps of incorporating (step (i)), and measuring (step (ii)), the standard set of wavelengths is obtained by creating a table of approximate wavelengths derived from a first, a second or both the first and the second wavelength calibration table, wherein a pixel number of a linear diode array of the first apparatus and a pixel number of a second linear diode array of the second apparatus must be within less than or equal to about ±N pixel of a reference pixel number of the first apparatus, where, N is a number of pixels that encompass a range of wavelengths of no more than about ±20 nm, wherein the reference pixel number of the first apparatus is associated with a known wavelength of electromagnetic radiation.

The present invention provides the method (C), above, wherein the wavelength calibration table for the first apparatus or the second apparatus is obtained by:
  (i) projecting a first electromagnetic radiation of known wavelength, onto a first pixel of a first linear diode array of the first apparatus, or a second linear diode array of the second apparatus;
  (ii) using a second electromagnetic radiation of known wavelength, the second electromagnetic radiation having a different wavelength than the first electromagnetic radiation, projecting the second electromagnetic radiation onto a second pixel of the first or the second linear diode array;
  (iii) identifying the first and second pixels within the first or the second linear diode array;
  (iv) calculating a pixeldispersion for the first or the second linear diode array; and
  (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

The present invention also provides the method (C) above, wherein the wavelength calibration table for the first or the second apparatus is obtained by:
  (a) projecting a known wavelength of electromagnetic radiation, onto a pixel in a linear diode array of the first apparatus, or the second apparatus;
  (b) identifying pixel number of the pixel;
  (c) assigning a wavelength to each pixel within the linear diode array to produce the first, second, or both the first and the second wavelength calibration table using a predetermined pixeldispersion, the known wavelength of electromagnetic radiation and the pixel number.

The present invention also includes the method (D) above, wherein a statistical technique selected from the group consisting of simple linear regression, multiple linear regression, and Multivariate data analysis, is used to process absorbance measurements for the development of the at least one primary calibration algorithm, wherein the Multivariate data analysis is selected from the group consisting of Principal Component Analysis, Principal Component Regression, Partial Least Squares regression, and Neural Network.

The present invention also provides the method (D), above, wherein in the steps of incorporating (step (i)), and measuring (step (ii)), the standard set of wavelengths is obtained by creating a table of approximate wavelengths derived from a first, a second or both the first and the second wavelength calibration table, wherein a pixel number of a linear diode array of the first apparatus and a pixel number of a second linear diode array of the second apparatus must be within less than or equal to about ±N pixel of a reference pixel number of the first apparatus, where, N is a number of pixels that encompass a range of wavelengths of no more than about ±20 nm, wherein the reference pixel number of the first apparatus is associated with a known wavelength of electromagnetic radiation.

The present invention pertains to the method (D), above, wherein the wavelength calibration table for the first apparatus or the second apparatus is obtained by:
  (i) projecting a first electromagnetic radiation of known wavelength, onto a first pixel of a first linear diode array of the first apparatus, or a second linear diode array of the second apparatus;
  (ii) using a second electromagnetic radiation of known wavelength, the second electromagnetic radiation having a different wavelength than the first electromagnetic radiation, projecting the second electromagnetic radiation onto a second pixel of the first or the second linear diode array;
  (iii) identifying the first and second pixels within the first or the second linear diode array;
  (iv) calculating a pixeldispersion for the first or the second linear diode array; and
  (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

The present invention also provides the method (D), above, wherein the wavelength calibration table for the first or the second apparatus is obtained by:

(a) projecting a known wavelength of electromagnetic radiation, onto a pixel in a linear diode array of the first apparatus, or the second apparatus;

(b) identifying pixel number of the pixel;

(c) assigning a wavelength to each pixel within the linear diode array to produce the first, second, or both the first and the second wavelength calibration table using a predetermined pixeldispersion, the known wavelength of electromagnetic radiation and the pixel number.

In a further aspect of the invention, a Second Apparatus that was calibrated by "Calibration Algorithm Transfer" but is no longer in control, can be "Recalibrated" using a Set of Calibrators that was assigned absorbances or absorbance values by the First Apparatus, which was known to be in control. The present invention also provides a method for Recalibration of the First Apparatus in the same way as any Second Apparatus.

The inventor has also found that the process of Calibration Algorithm Transfer and subsequent determination of analyte concentration can be accomplished by using an order of derivative of the absorbance in the Primary Calibration Algorithm, where absorbance correction or "Photometric Correction" may not be necessary, provided that the order of derivative of absorbance used in the Primary Calibration Algorithm at the selected wavelength(s) does not contain significant inter-apparatus variability as may be seen in the absorbances at the same wavelength(s). Absorbance variability between apparatus can be minimized in certain "Sections of the Absorbance Spectra," by using an order of derivative of the absorbance.

The present invention provides a method to provide a simple reliable method of using primary calibration algorithms in a second apparatus that do not require representative samples for which the apparatus was designed. Rather, the standard samples used to calibrate a second apparatus can be any stable samples that produce a range of absorbances at all relevant wavelengths.

The prior art teaches how to calibrate a first apparatus using a derivative of absorbance, but the inventor is not aware of any prior art that teaches how to obtain an analyte concentration from a second apparatus, by using a calibration algorithm derived from the derivative of absorbances, and obtained on the first apparatus.

This summary of the invention does not necessarily describe all necessary features of the invention but that the invention may also reside in a sub-combination of the described features.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF INVENTION

Figure 1:
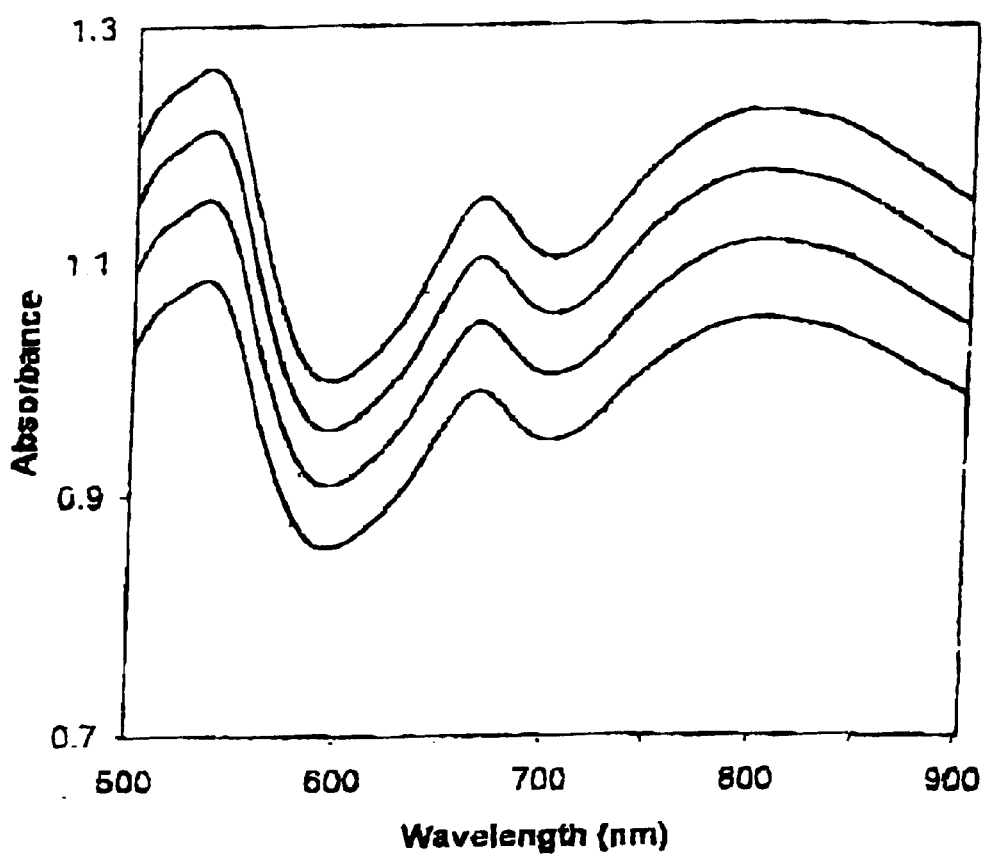
FIG. 1 is a graphic representation of the absorbance spectra of four different synthetic calibrators, tested on the First Apparatus.

The following description is of a preferred embodiment by way of example only and without limitation to the combination of features necessary for carrying the invention into effect.

The method used to calibrate a first apparatus wherein the apparatus can be used to measure the concentration of at least one analyte is referred to as Primary Calibration. Primary Calibration is a complex process and is described under the title "Primary Calibration." Due to its complexity, performance of primary calibration on every apparatus is not desirable.

The present invention provides a simple alternative that allows an apparatus to function as though it was calibrated by the process of primary calibration, whereby the apparatus need not be calibrated in the same way in which the first apparatus was calibrated, that is by conducting a primary calibration. It is preferred that the first and second apparatus are similar. There are several aspects of this invention including:

i) Calibration Algorithm Transfer
ii) Recalibration
iii) Calibration, and
iv) Calibration of a Second Apparatus optionally using data pre-processing.

These four, as well as other, aspects of the invention are described in detail below.

Where calibrators are required for the invention, the calibrators are preferably synthetic calibrators, but other calibrators may be used as will be obvious as the invention is described in details. With respect to synthetic calibrators, part of the process of calibration algorithm transfer teaches one method of assigning absorbances to a batch of calibrators. It is preferred that an apparatus, for example, the first apparatus, that is in control be used.

A fifth aspect of the invention that includes use of a second apparatus is as follows:

v) Assigning Absorbances to a Second Batch of Calibrators Methods for assigning absorbances to a second batch of calibrators are described, wherein the original primary calibration algorithm(s) may be used whereby the process of primary calibration could be avoided.

The first and second apparatus use absorption of electromagnetic radiation to measure analytes in one or more samples. Throughout this application reference is made to measurements through absorption of electromagnetic radiation. While this is preferred, it should be understood that the present invention is not limited to absorption and measurements by other means such as reflectance or transmittance are also within the scope of the present invention.

Technical terms used in the disclosure are defined below for clarification.

By "Actual Wavelength" it is meant a wavelength from the wavelength calibration table.

By "Analyte" it is meant a substance being measured in a sample.

By "absorbance", it is meant a measurement calculated from the amount of light reflected or transmitted by a sample, as would be known to one of skill in the art.

By "Assigned Absorbances" or "Assigned Absorbance Measurement" or "Assigned Absorbance Values" it is meant the interpolated absorbances of calibrators whose absorbances are measured on the first apparatus when it is in control, or the adjusted interpolated absorbances of a second batch of calibrators.

By "Actual Absorbance" or "Measured Absorbance" it is meant the absorbance value, or absorbance measurement, or simply absorbance of a sample or calibrator provided by the apparatus at a wavelength from the wavelength calibration table of the apparatus.

By "Adjusted Interpolated Absorbance" it is meant the value of the interpolated absorbance after photometric correction is applied specifically to the interpolated absorbance.

By "Blood Bag Tubing" it is meant the tubing connecting a first plastic bag that contains whole blood and a second plastic bag that may contain plasma obtained from the first bag. The tubing and bags may be made from transparent or translucent flexible plastic.

By "Calibration Set", a "Set of Calibrators", or "Calibrators" it is meant two or more calibrator samples. Any type of Calibrators suitable for producing one or more first linear regression equations based on interpolated absorbances obtained using a first apparatus that is in control and interpolated absorbances obtained using a Second apparatus, may be used.

By "Calibration" it is implied the process of incorporating at least one primary calibration algorithm in an apparatus that does not have at least one valid primary calibration algorithm incorporated, plus the process of establishing and incorporating one or more second linear regression equations in the apparatus. Calibration does not require the first apparatus. Typically, calibration of an apparatus is required when the apparatus does not have at least one valid relevant primary calibration algorithm incorporated.

By "Calibration Algorithm Transfer" or "Transferring a Calibration Algorithm" it is meant the process of incorporating at least one primary calibration algorithm and one or more first linear regression equation within a second apparatus. A first linear regression equation is necessary for performance of photometric correction. Calibration algorithm transfer requires the first apparatus, a second apparatus, and a set of calibrators. An aspect of this invention, which is discussed separately, is calibration algorithm transfer with the optional use of photometric correction, and other forms of data pre-processing.

"Data Pre-processing" is any mathematical manipulation of spectrophotometric data, which is can be used to facilitate measurement of an analyte on an apparatus, including a first, second, or both, apparatus. Examples of data pre-processing, which should not be considered limiting in any way are: calculation of absorbance of light transmitted through or reflected from a sample; calculation of interpolated absorbances; smoothing of absorbances; calculation of a first and higher order derivative of absorbance; multiplicative scatter correction; data transformation; photometric correction. It should be understood that any one or more forms of data pre-processing can be used prior to development of a calibration algorithm, and any one or more forms of data pre-processing can be used on the data from a second apparatus, prior to applying the calibration algorithm for calculating the concentration of an analyte. A non-limiting example of smoothing includes averaging of data.

"Data Transformation" is any mathematical technique that can be applied to either the spectrophotometric data or the analyte concentration data. Examples, which should not be considered limiting in any way, are Fourier Transformation of spectrophotometric data, and calculation of the log or anti-log of an analyte concentration. It should be understood that smoothing can also be considered as data transformation, for example when the Savitzky-Golay method (Savitzky and Golay 1964, Anal. Chem., 36:1627–1638). is used.

By "Derivative of Absorbance" it is meant an order derivative of the absorbance spectrum. Zero order derivative of absorbance is the measured absorbance. The first order derivative of absorbance at a particular wavelength is the slope of the absorbance spectrum at that wavelength; the second order derivative of absorbance at a particular wavelength is the slope of the first derivative absorbance spectrum at the wavelength. Higher order derivative (third, fourth etc.) of absorbance can similarly be obtained by taking the slope of the derivative absorbance spectrum of the order immediately below (second, third etc.) Methods of calculating a derivative of absorbance at a particular wavelength are well known by those skilled in the art. The calculation of the first derivative of absorbance at a particular wavelength may consist in taking the difference in absorbances at the two wavelengths that encompass the wavelength of interest. Other methods of calculating derivative of absorbance may use the absorbances at several different wavelengths, where smoothing is an integral part of the derivative process. It should be understood that with a greater degree of smoothing, there is also a greater loss of signal details in the absorbance spectrum or derivative of absorbance spectrum. The minimum number of wavelengths that may be used to calculate a derivative of absorbance is two wavelengths. Smoothing, data transformation, and calculation of order derivatives of absorbances are non-limiting examples of data pre-processing. Other forms of data pre-processing may be performed either before or after calculation of an order derivative of absorbance, and include but are not limited to multiplicative scatter correction.

By "Discrete wavelength" it is meant a single wavelength.

By "First Absorbance" it is meant the absorbance measured on the first apparatus.

By "First Apparatus" it is meant an apparatus used to develop the at least one primary calibration algorithm.

"A First Linear Regression Equation" is an equation of the form "y=mx+c" obtained from the absorbances obtained from a set of calibrators on both the first apparatus, and a second apparatus during the process of calibration algorithm transfer, where "m" is the slope and "c" is the y-intercept.

By "Full spectrum" it is meant continuous sections of the absorbance spectrum or derivative of absorbance spectrum, up to and including a complete spectrum. For example, which is not to be considered limiting in any manner, the absorbance of primary calibrators over a full spectrum may be used to determine a primary calibration algorithm, for example, using Partial Least Squares ("PLS") analysis or Principal Component Analysis (PCA). It should be understood that sections of a full spectrum may also be used for PLS analysis or PCA.

By "Interpolated Absorbance," it is meant the absorbance value for a specific wavelength of a standard set of wavelengths. If the specific wavelength of the standard set of wavelengths is the same as the wavelength already assigned to a pixel of a linear diode array, i.e., a wavelength of the wavelength calibration table, then the interpolated absorbance is the same as the measured absorbance. However, if the specific wavelength is different from the wavelength assigned to a pixel, then the value of interpolated absorbance, at the specific wavelength, is estimated from the measured absorbance values of at least two adjacent pixels whose wavelengths encompass one or more standard wavelengths. It should be noted that the term "Interpolated Absorbance" is applied when the wavelength calibration table is the same as the standard set of wavelengths, and also when the wavelength calibration table is different from the standard set of wavelengths, i.e., whether or not there was a need for interpolation.

An apparatus is the to be "In Control" when that apparatus produces absorbance measurements that are within a predetermined acceptable range for one or more given wavelengths, or predicted analyte values that are within a predetermined acceptable range for one or more analytes.

By "Interferent" it is meant an analyte whose presence in a sample, particularly a serum or plasma sample, interferes with the determination of the presence and/or quantification of another analyte(s).

By "Mapping" it is meant the process of associating an interpolated absorbance value with a standard wavelength.

"Multiplicative Scatter Correction" (also known as multiplicative signal correction) is a mathematical technique that may be used to remove at least some of the light scattering effect in the spectrophotometric data obtained from a sample set. The technique rotates each spectrum so that it fits as closely as possible to the mean spectrum. The technique is described in more details in: Martens, H and Naes, T (Multivariate Calibration, 1993, Published by John Wiley & Sons); and Osborne, B. G., Fearn, T & Hindle, P. H. (Practical NIR Spectroscopy with Applications in Food and Beverage Analysis, 1993, Published by Longman Scientific & Technical), both of which are incorporated herein by reference. It should be understood that the mean spectrum for a sample set can be obtained after combining one or more sample measurements obtained from one or more than one apparatus.

By "Optimizing Primary Calibration Wavelengths" it is meant a process of choosing the Primary Calibration Wavelength(s) that exhibits measurable changes in the derivative absorbance as a function of analyte concentration (measurable analyte signal) and which also exhibits a low variability, that is to say a variability that is below a predetermined value in the derivative of absorbance between apparatuses for a given analyte concentration, for each of the optimized calibration wavelengths. Examples of low variability values, include values that translate into less than 20%, preferably less than 10%, and more preferably less than 5% coefficient of variation (CV) of predicted analyte concentration, where:

$$\%CV=([\text{Standard Deviation/Mean}]\times 100\%).$$

Figure 9:
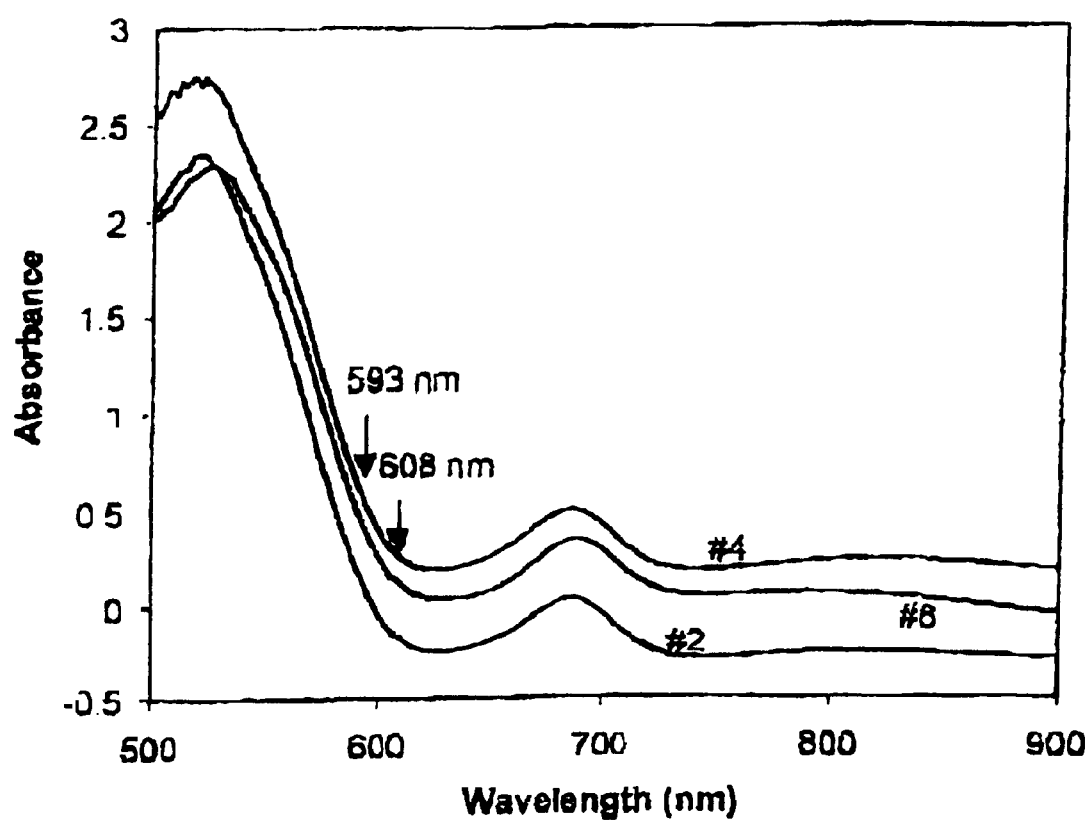
FIG. 9 is a graphic representation of the absorbance spectra of the same synthetic fluid tested on 3 different apparatuses (#2, #4, #6) using a standard set of wavelengths.
Figure 10:
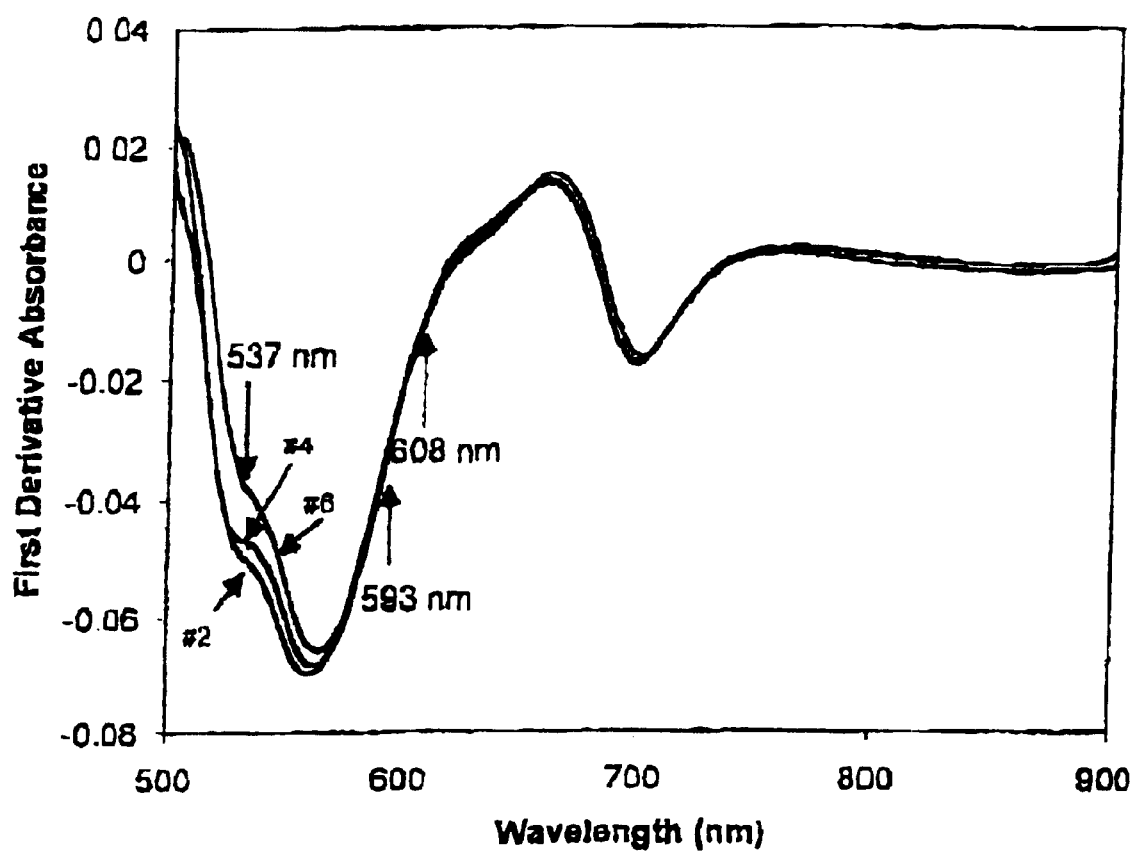
FIG. 10 is a graphic representation of the first derivative of absorbance spectra of the same synthetic fluid tested on 3 different apparatuses (#2, #4, #6) using a standard set of wavelengths; the absorbance spectra are shown in FIG. 9.
Figure 16:
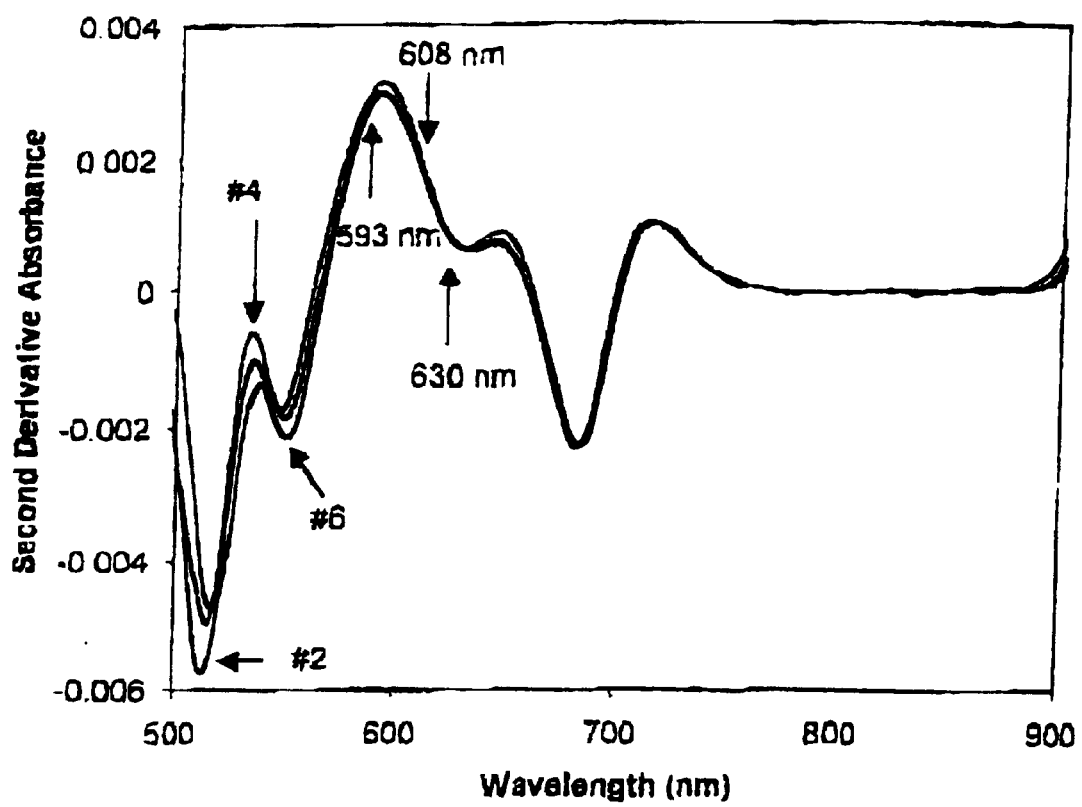
FIG. 16 is a graphic representation of the second derivative of absorbance spectra of the same synthetic fluid tested on 3 different apparatuses (#2, #4, #6) using a standard set of wavelengths.
Figure 19:
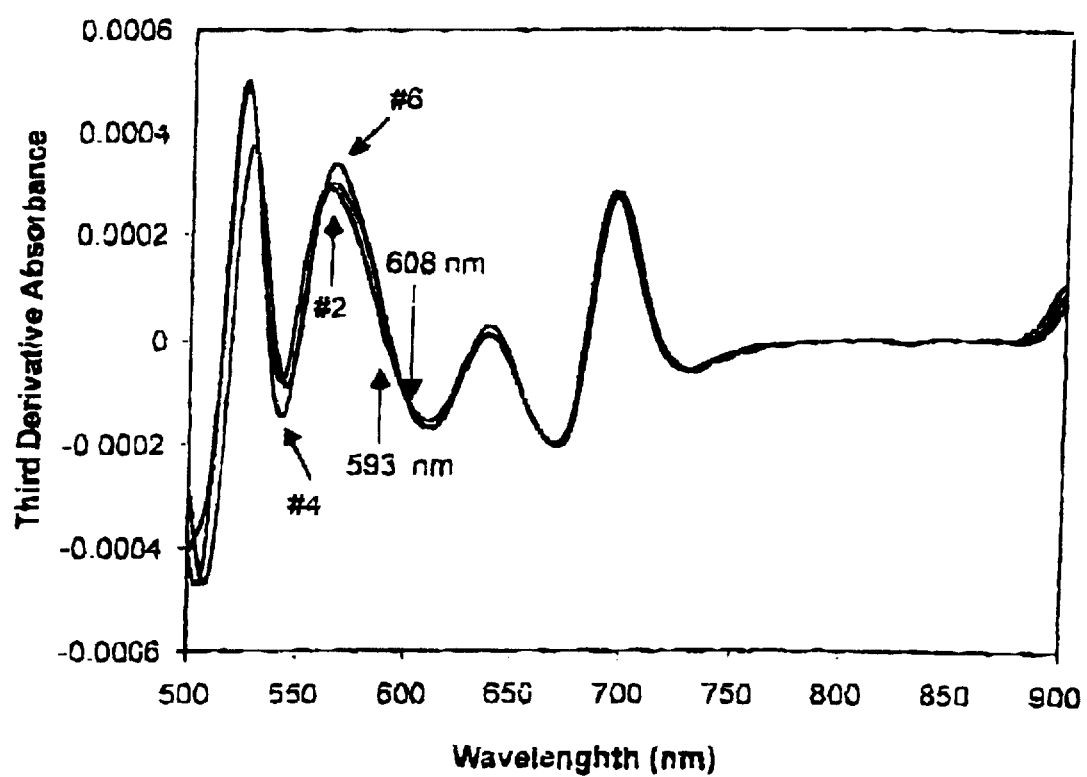
FIG. 19 is a graphic representation of the third derivative of absorbance spectra of the same synthetic fluid tested on 3 different apparatuses (#2, #4, #6) using a standard set of wavelengths. The wavelengths identified as 593 nm and 608 nm were used in the calibration algorithm of Example 2 for hemoglobin when the first derivative of absorbance was used.

Optimization of primary calibration wavelengths may be accomplished by one of two methods that comprises:

1) Plot the absorbance spectra vs the standard set of wavelengths of a sample tested on two or more apparatus, as exemplified in FIG. 9; plot the derivative of absorbance of the sample tested on two or more apparatus, as exemplified in FIG. 10, FIG. 16 and FIG. 19 for the first, second and third derivative or absorbance respectively. Visually select one or more wavelength of a standard set of wavelengths that exhibit a low variability in the derivative of absorbance and also with measurable analyte signal, preferably with least variability in the derivative of absorbance and also with measurable analyte signal.

2) When multiple linear regression is used to develop the primary calibration algorithm, a method used to select wavelengths that show minimum variability in the absorbance, or derivative of absorbance, is to test the primary calibration set on two or more apparatus, preferably apparatus that exhibit the expected limit of absorbance and wavelength variability, and use the data from all the apparatus in the primary calibration data set. An example of a software tool used for preparing primary calibration algorithms is StatView™ that is used to create calibration algorithms by a process called step-wise multiple linear regression. In step-wise multiple linear regression, absorbance or derivative of absorbance measurements for all the wavelengths may be presented to the StatView™ program, and only the wavelengths at which the criteria of changes and low variability in derivative of absorbance are met would be selected for the primary calibration algorithm based upon how well a primary calibration algorithm for a particular analyte predicts the analyte concentrations of the samples of the primary calibration set. Further, wavelengths which contribute least to the calibration algorithm may be eliminated until at least the desired number of wavelengths are left. After the wavelength(s) is/are selected, preferably only the data generated from a first apparatus should be used to develop the final primary calibration algorithm, using the predetermined wavelength(s). Preferably more than the derived number of wavelengths are submitted to StatView™ software, with data only from the first apparatus, and further elimination of wavelengths not meeting the criteria should be performed until the desired number of wavelengths remain.

By "Primary Calibration" it is meant a process used to develop a primary calibration algorithm for a first apparatus for an analyte or optionally for more that one first apparatus. The sample set used for calibration is relatively large, and the samples are natural or very close to natural samples. The primary calibration set should include all the variability expected in a sample, in order to develop robust calibration algorithm(s). Furthermore, one, or more than one sample of the primary calibration set could be measured on one or more than one first apparatus and combined, in order to develop a more robust calibration algorithm(s) that also includes inter-apparatus variability. Such a calibration algorithm would be developed using a combination of measurements obtained from one, or more than one, similar apparatus. Any form of statistical data analysis and optionally any form of data pre-processing, for example but not limited to, smoothing, calculation of first and higher order derivative of absorbance, photometric correction, data transformation, interpolation of absorbance, or multiplicative scatter correction, may be used, depending on the required accuracy of the analyte prediction. For example, by including data from more than one first apparatus, a lower level of precision and hence a lower level of accuracy (poor precision translates into poor accuracy) may be obtained across many second apparatus. Such a type of primary calibration would be suitable if a simple yes/no answer to the presence of an analyte in a sample is all that is required, and is within the scope of this invention.

In another embodiment, a smaller set of samples like those of the primary calibration set, or a subset of the primary calibration set, or both, can be measured on a second apparatus, and the data combined with some or all of the original data from the primary calibration set, to develop one, or more than one, "upgraded primary calibration algorithm".

By a "Primary Calibration Set" it is meant the samples used for primary calibration.

By "Primary Calibration Wavelength(s) it is meant the wavelength(s) used in a primary calibration algorithm.

By "Pixeldispersion" it is meant, the wavelengths encompassed by two adjacent pixels of a linear diode array, usually measured in nanometers (nm) per pixel. For example, if two lasers of 600 nm and 900 nm are used for wavelength calibration, and they are projected on pixel 20 and pixel 220 respectively, that means 300 nm (i.e., 900–600 nm) are encompassed by 200 pixels (i.e., 220–20 pixels). Therefore the Pixeldispersion is calculated to be 1.5 nm per pixel (i.e., 300 nm divided by 200 pixels). The assigned Pixeldispersion may be predetermined by the steps comprising:

(i) Projecting a first electromagnetic radiation of known wavelength, onto a first pixel of a linear diode array preferably towards one end of the linear diode array;

(ii) Using a second electromagnetic radiation of a known wavelength but different from the first electromagnetic radiation, projecting the second electromagnetic radiation onto a second pixel that is preferably towards the opposite end of the linear diode array;

(iii) Identifying the first and second pixels within the linear diode array;

(iv) Calculate the Pixeldispersion in nanometers per pixel or any wavelength units per pixel as described above; and Use the Pixeldispersion value calculated in step (iv) as the predetermined Pixeldispersion, or repeating steps (i) to (iv) on one or more apparatus with linear diode arrays, preferably the linear diode arrays of the apparatus are similar, and use the average pixeldispersion as the predetermined Pixeldispersion.

By "Photometric Correction" or "Absorbance Adjustment" it is meant an adjustment made to an absorbance of a sample tested on one apparatus, to make it appear as if the sample was tested on another apparatus. The amount of photometric correction is determined by the slope and y-intercept of the first and second linear regression equations. The resulting absorbance after photometric correction is referred to as Adjusted Absorbance or Corrected Absorbance.

By "predicted value," it is meant a value of an analyte obtained when the primary calibration algorithm for the analyte is applied to spectrophotometric data, with optional pre-processing, of a sample. A primary calibration algorithm is an equation comprising a predicted value of the analyte as the dependant variable and a constant, and one or more terms, preferably a linear summation of the constant and the terms. Preferably each term is the product of a constant and an independent variable as shown in the examples. It should be understood that the use of non-linear primary calibration algorithms is within the scope of this invention. The independent variable is the optionally pre-processed absorbance of the sample at a standard wavelength.

By "Relevant Primary Calibration Algorithm" it is meant the primary calibration algorithm for a particular analyte, particularly with respect to the one installed in an apparatus. A primary calibration algorithm is required for each analyte, regardless of the wavelength or wavelengths used in the primary calibration algorithm(s), and one or more primary calibration algorithms may be installed in an apparatus.

By "Recalibration" it is meant a process of establishing and incorporating one or more Second Linear Regression Equations in an apparatus that already has at least one valid primary calibration algorithm incorporated. Typically, recalibration of an apparatus is required when the apparatus is not In Control.

By "Sample" or "Samples" it is meant a biological or non-biological fluids, or a solid exhibiting one or more properties that may be measured spectrophotometrically. A sample typically comprises one or more analytes. A sample is characterized in that the energy of one or more wavelengths can be either transmitted, absorbed, scattered, reflected, or a combination thereof, by an analyte within the sample. Examples of a sample include, but are not limited to, a calibrator, serum or plasma, a body part, for example but not limited to, a finger, arm, ear lobe, or a pharmaceutical tablet.

By "Smoothing" a curve, for example an absorbance spectrum, it is meant applying a mathematical function to the digital data to produce a "continuous spectrum" and thereby reduce the "noise" in the spectrum. Various degrees of smoothing may be applied to a curve. The loss of analyte signal may be a price paid for smoothing.

By "Second Apparatus" it is meant an apparatus that is allowed to function like a first apparatus, whereby the second apparatus need not be calibrated in the same way in which the first apparatus was calibrated, i.e., by conducting a primary calibration. Samples similar to those of the primary calibration set, or a subset of the primary calibration set, may be measured on a second apparatus to develop an upgraded primary calibration algorithm, if desired.

"A Second Linear Regression Equation" is an equation of the form "y=mx+c" obtained from the interpolated absorbances obtained from a set of calibrators on both the first apparatus and any other apparatus during the process of "Recalibration," or "Calibration" where "m" is the slope and "c" is the y-intercept.

By "Second Absorbance" it is meant the absorbance measured on the second apparatus.

By a "Section of the Absorbance Spectra" it is meant absorbances at more than one wavelength where the wavelengths are in succession.

By a "Standard Set of Wavelengths" it is meant a set of wavelengths used by all apparatus in conjunction with the apparatus-specific wavelength calibration table, used to generate interpolated absorbances from the measured or actual absorbances. The actual absorbances of a sample tested on an apparatus are measured at wavelengths from the wavelength calibration table, and the actual absorbances may be interpolated and mapped onto the standard set of wavelengths. The primary calibration algorithm(s) is preferably applied to the mapped absorbances, but may be applied to the actual absorbances, particularly when the wavelength calibration table and the standard set of wavelengths are the same. Without wishing to be limiting in any manner, an example of a standard set of wavelengths includes 500 to 1100 nm, in increments of 2 nm. However, other wavelength ranges and increments may be used as required, and as would be known by one of skill in the art. The range of the standard set of wavelengths may be derived from the wavelength calibration table, and the increment may be obtained by trial and error. The standard set of wavelengths may also be obtained by establishing a set of wavelengths common to the wavelength calibration tables of both first and second apparatus. Also, the standard set of wavelengths may be obtained by establishing a set of wavelengths that approximate the wavelengths of the wavelength calibration tables of both first and second apparatus.

By a "Standard Wavelength" it is meant a wavelength from the standard set of wavelengths.

By a "Validation Set" it is meant the samples used for testing the prediction accuracy of a primary calibration algorithm, and may also be used for testing the robustness of the primary calibration algorithm.

By "Vessel" it is meant any transparent or translucent container capable of holding a sample, preferably fluid, to enable measurement of absorbance, reflectance, or both absorbance and reflectance of radiation in the sample. Examples of vessels include, but are not limited to, pipette tips, tubing, cuvettes, labeled test tubes, unlabeled test tubes, blood bag tubing, any transparent sample container, and any translucent sample container. In the case of a solid sample, a sample holder may be required instead of a Vessel.

By "Valid Primary Calibration Algorithm" it is meant that the apparatus is in control, particularly for the analyte predicted by the primary calibration algorithm.

By "Wavelength Calibration" it is meant the calibration of a Linear Diode Array detector, Charged Coupled Detector, or any other like device, of a spectrophotometer, wherein wavelengths are assigned to each pixel in the Linear Diode Array, or Charged Coupled Detector.

By "Wavelength Calibration Table" it is meant a table that provides the actual wavelength corresponding to or assigned to each pixel, which is a result of the wavelength Calibration.

The present invention provides a method to calibrate a second apparatus using a Primary Calibration algorithm(s) developed for one or more than one First Apparatus. Primary calibration may be developed on the first apparatus using known techniques. The present invention also provides a method for Recalibrating a second apparatus, and if required, recalibration of the First Apparatus.

It is preferred that the Primary Calibration Algorithm(s) and the assigned absorbance measurements of calibrators are stored on a suitable medium, for example, electronically stored, permitting ready transfer to the Second Apparatus.

It is also preferred that the samples used for the Primary Calibration, i.e., the primary calibration set, and the calibrators, are placed within vessel having optical properties substantially similar. If a body part is used as a sample, it is regarded as the vessel. Examples of vessel include, but are not limited to, a pipette tip, a labeled test tube, an unlabeled test tube, blood bag tubing, any transparent container, any translucent container, a finger, an ear, and arm or other body part. The sample can be liquid for example, a biological fluid, including but not limited to bodily fluids, serum or plasma, or non-biological, for example but not limited to synthetic calibrators or a beverage, or solid, for example, which is not to be considered limiting in any manner, cheese or a medicament, for example a pharmaceutical tablet. Furthermore, any type of calibrator suitable for producing a set of first linear regression equations based on assigned absorbances obtained from a First apparatus and interpolated absorbances from a Second apparatus, may be used. For example, a set of calibrators may comprise translucent substances such as fiberglass which may vary in thickness, color, or finish, depending on the type of analyte to be measured. The calibrators may also comprise solid particles in liquid suspension, e.g., polystyrene beads in a buffer of similar density as the polystyrene beads. Calibrators may also comprise fat emulsion, for example fat particles in suspension. Calibrators may also comprise colored glass of varying thickness and finish. In any event, the calibrators must be capable of producing a suitable set of first linear regression equations for relevant wavelengths, obtained from a First Apparatus and a Second Apparatus.

The apparatus are used to measure concentrations of analytes using electromagnetic radiation, most preferably using near infrared radiation and the adjacent visible radiation spectrum, for example, but not limited to, any suitable wavelength from about 300 nm to about 2500 nm, preferably from about 500 nm to about 1100 nm, and more preferably from about 500 nm to about 800 nm.

A standard set of wavelengths may be used as required for standardizing the absorbance data to be used for obtaining a primary calibration algorithm. The actual set of wavelengths provided by an apparatus depends on the manner in which the wavelength calibration is performed. Further, a standard set of wavelengths and the method used to generate them depends on the accuracy requirement for analyte prediction. In order for a second apparatus to use the primary calibration algorithm(s) developed on a first apparatus, it is preferred that each apparatus should provide the same set of actual wavelengths. An example of a way whereby one or more apparatus can be made to operate as if they have the same wavelengths, which is not to be considered limiting in any manner, is provided under the title "Wavelength Calibration."

A linear wavelength table comprising a known set of wavelengths that fall within the required range and with equal increments, may be used as a standard set of wavelengths. For example, the range may be 500 nm to 1100 nm, in increments of 2 nm. The absorbance values measured at the actual wavelengths assigned to each pixel of the apparatus, i.e., the wavelength calibration table, may be interpolated and mapped onto the standard set of wavelengths, thereby allowing different apparatus the appearance of having been provided the same set of actual wavelengths. The number of wavelengths in the standard set of wavelengths do not have to be equal to the number of pixels in the diode array. For example, the number of pixels may be more or less that the number of wavelengths, but it is preferred that the number of wavelengths should approximate the number of pixels. In a preferred embodiment, similar linear diode arrays with the same number of pixels should be used.

The following is a preferred embodiment of the apparatus used in the present invention:

Apparatus:

The preferred embodiment of the apparatus is described both in general terms and specific requirements. The present invention provides an apparatus that may be used for measuring the concentration of an analyte in a sample. An example, which is not to be considered limiting, of such an apparatus and the primary calibration algorithms is given in WO9838961. It is preferred that apparatus have similar components. The major components of an apparatus may comprise:

1. A spectrophotometer comprising:
    A diffraction grating, focussing lenses, slits, and a linear diode array detector (sometimes referred to as simply a linear diode array). It is preferred that spectrophotometers have similar components, including the number of pixels in the linear diode array. It should be understood that other arrays, for example but not limited to CCD (charged coupled detector) arrays, may also be used as described herein. The spectrophotometer can operate in a single or dual beam configuration. If the spectrophotometer is a dual beam spectrophotometer, one of the beams acts as a reference beam and the other is the sample beam; two shutters are required to facilitate the sample and reference measurements.
2. A light source
3. A power supply
4. A sample holder with light coming from the lamp through an optical fiber, and light transmitted through the sample to the spectrophotometer via a second optical fiber.
5. A circuit board that includes an amplifier and an analog to digital converter, is required to interface the linear diode array detector and a microprocessor. The Primary Calibration Algorithm and other information like the wavelength calibration table may be imbedded in an EPROM.
6. Software that may comprise features for: utilizing the calibration package; interpolating absorbances; mapping absorbances to a standard set of wavelengths; smoothing; creating derivatives of absorbances; calculating analyte concentrations.

Differences in absorbances for the same sample occur between apparatus for a number of reasons including:

1. The corresponding pixels in similar linear diode array detectors respond differently to the same amount of light.
2. The incremental wavelength per pixel or pixeldispersion may vary between any two similar linear diode array detectors.
3. The physical distances between pixels in the linear diode array are not always constant within a linear diode array, and also between similar linear diode arrays.
4. Spectrophotometers contain wavelength inaccuracies, depending on the method used for wavelength calibration. One illustration is provided in Example 6.
5. Variability in other components of the spectrophotometers, e.g., the diffraction grating, filters, and slits.

The present application is directed to providing a method for calibrating an apparatus for an analyte involving the steps of:

A) WAVELENGTH CALIBRATION: A process of wavelength calibration provides a wavelength calibration table that gives the wavelengths assigned to each pixel. The linear diode array detector comprises of pixels, for example, which should not be considered limiting in any way, 128 or 256 pixels assembled in a linear array. In order that different apparatus would appear to have the same wavelength calibration table, the absorbances of a sample may be interpolated and mapped unto a standard set of wavelengths. It is preferred that the same standard set of wavelengths be used with each apparatus. When the disclosure refers to "measured at a standard set of wavelengths," it should be understood that "interpolated absorbances mapped to a standard set of wavelengths" is implied, unless all apparatus have the same wavelength calibration table, or the standard set of wavelengths are an approximation of the wavelengths in the wavelength calibration table of a first, second, or both the first and second apparatus, in which case the step of interpolation is automatically eliminated.

B) PRIMARY CALIBRATION: Primary calibration is a process used to develop a primary calibration algorithm for a first apparatus for an analyte. The sample set used for primary calibration is relatively large, and the samples are natural or very close to natural samples and should include all the variability expected in a sample. For each unique analyte a unique primary calibration algorithm is required, therefore, an apparatus may comprise more than one primary calibration algorithm depending on the number of analytes to be measured. Variability among similar apparatus can also be included into the primary calibration algorithm by measuring one, or more than one, of the primary calibration set on one or more than one first apparatus, and developing the primary calibration algorithm using a combination of measurements obtained from each of the apparatus. Samples similar to those of the primary calibration set, or a subset of the primary calibration set, may be measured on a second apparatus to develop an upgraded primary calibration algorithm, if desired.

C) VALIDATION: After the calibration algorithm is developed for an analyte, a second sample set is used to validate the calibration algorithm. If enough variability is not included in the primary calibration set, the analyte predictions for the validation set may correlate poorly with the actual analyte concentrations. Proper validation is a test of robustness of the primary calibration algorithm.

D) CALIBRATION ALGORITHM TRANSFER: This section describes the process of calibration algorithm transfer. It is the process of incorporating at least one primary calibration algorithm and optionally one or more first linear regression equation within a second apparatus. A first linear regression equation is necessary for performance of photometric correction. Calibration algorithm transfer requires the first apparatus, a second apparatus, and optionally a set of calibrators.

E) RECALIBRATION: This section describes the sequel to calibration algorithm transfer to a second apparatus, requiring at least two calibrators with absorbance values assigned to them by the apparatus used to develop the primary calibration algorithm, while the apparatus was in control. The first apparatus is not required, unless it is the apparatus being recalibrated, and the primary calibration algorithm will have already been incorporated in the second apparatus. By recalibration it is meant a process of establishing and incorporating one or more Second Linear Regression Equations in an apparatus that already has at least one valid primary calibration algorithm incorporated. Typically, recalibration of an apparatus is required when the apparatus is not in control.

F) CALIBRATION: This section describes the process of incorporating at least one primary calibration algorithm in an apparatus that does not have at least one valid primary calibration algorithm incorporated, plus the optional process of establishing and incorporating one or more second linear regression equations in the apparatus. Calibration does not require the first apparatus, unless it is the apparatus being calibrated. Typically, calibration of an apparatus is required when the apparatus does not have at least one valid relevant primary calibration incorporated.

G) CALIBRATION OF A SECOND APPARATUS OPTIONALLY USING DATA PRE-PROCESSING: Determination of analyte concentration in a sample in a second apparatus may be accomplished by using an order derivative of absorbance, including zero order, optionally combined with other forms of data pre-processing of the absorbance of the sample. Photometric correction may or may not be necessary, depending on the required accuracy of the predicted analyte concentration. Any statistical technique may be used to derive the primary calibration algorithm, for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks. Examples of data pre-processing which should not be considered limiting in any way, include smoothing, deriving a first or higher order derivative of absorbance, interpolation of absorbance, multiplicative scatter correction, photometric correction, and data transformation, for example Fourier transformation. Preferably, the calibration algorithm is applied to the absorbance data of future samples after data pre-processing. While not necessary, it is preferred that the form or combination of forms of data pre-processing used in a second apparatus, should be the same as the form or combination of forms of data pre-processing used prior to primary calibration algorithm development.

H) SYNTHETIC CALIBRATION FLUIDS: Although calibrators can take on several different forms, provided that the set cover a range of absorbances at each relevant wavelength, whereby a linear regression equation between the absorbances from two apparatus can be established for each relevant wavelength. In a preferred embodiment, ready-to-use stable synthetic calibration fluids are used.

I) ASSIGNING ABSORBANCES TO A SECOND BATCH OF CALIBRATORS: This section describes the use of the first apparatus and a second apparatus to assign absorbance values to a new lot of synthetic calibrators.

J) CALIBRATION PACKAGE: When synthetic calibration fluids are used for recalibration or calibration of an apparatus, it is preferred that electronic information accompany the synthetic calibration fluids in the form of a package. The calibration package may comprise the following essential components: (i) At least one primary calibration algorithm; (ii) Calibrators; and (iii) Assigned absorbances for calibrators. This section describes the contents of this package in a preferred embodiment.

These steps are described in more details below:

A) Wavelength Calibration

A laser of known wavelength or electromagnetic radiation transmitted through a band-pass filter of know wavelength, is projected onto any pixel in a linear diode array. It should be understood that the electromagnetic radiation should not be restricted to a laser or a band-pass filter, and other sources of monochromatic electromagnetic radiation may be used. It should also be understood that the electromagnetic radiation could impinge upon more that one pixel, and that the relative position of peak intensity of the electromagnetic radiation may be determined mathematically by processes known to those skilled in the art. Further, the peak intensity may be positioned between any two pixels. The targeted pixel is preferably towards one end of the spectrum. A second laser of known wavelength or electromagnetic radiation transmitted through a second band-pass filter of known wavelength that is preferably projected towards the other end of the spectrum may be used and the pixel on which the beam is projected onto is identified. Since the number of pixels is known, one can determine the pixeldispersion. With the two known wavelengths and their corresponding pixels, and the pixeldispersion, one can generate a wavelength calibration table i.e., a table providing the discrete wavelength that is assigned to each pixel in the linear diode array. The absorbances at the wavelengths from the wavelength calibration table from one or more apparatus, can subsequently be interpolated and mapped unto a standard set of wavelengths. The absorbances at the two actual wavelengths that are on either side of the standard wavelength may be interpolated to produce an absorbance at a standard wavelength. This process may be repeated for each standard wavelength. This is, the preferred method for making the wavelengths provided by different apparatus, appear similar. Photometric accuracy depends in part on wavelength accuracy, and the prediction accuracy for an analyte concentration depends upon the photometric accuracy of the apparatus. In this respect, a qualitative method for an analyte where a yes/no answer is all that is desired does not require the same level of wavelength accuracy as a quantitative method for the same analyte. Futhermore, the calibration algorithm can be developed with more robustness by including data from one or more primary calibrators, measured on the first apparatus and one or more similar apparatus.

In this method of wavelength calibration, the first wavelength does not have to be projected upon the same pixel in the linear diode array of each apparatus, since the absorbances could be interpolated and mapped unto a standard set of wavelengths. The wavelength of a second laser or second band-pass filter is preferably chosen so that the beam of electromagnetic radiation is projected towards the other end of the linear diode array. It is preferred that the laser or band-pass filter be selected so that the beam of electromagnetic radiation is not projected too close to the end pixels in the linear diode array, if the resulting absorbances at the end pixels are noisy. It is also preferred that a bandpass filter is a narrow bandpass filter.

A second method to generate a wavelength calibration table is to project the first beam onto the same pixel of each linear diode array. When this method is used to generate a wavelength calibration table, the pixeldispersion is predetermined using two beams of different wavelengths, as described above. The pixeldispersion may be determined from a single spectrophotometer, but preferably the average value should be obtained from more than one like spectrophotometer. When the same pixeldispersion is used by each apparatus and the first beam is projected onto the same pixel number within each like linear diode array, the wavelength calibration table for each apparatus would be the same, and hence the wavelength calibration table may be used as the standard set of wavelengths. Consequently interpolation and mapping of absorbances to a standard set of wavelengths would automatically be eliminated. A second beam may be used to validate wavelength accuracy.

A third method to generate a wavelength calibration table is like the second method except that the first beam may be projected onto any pixel of the linear diode array. When the pixel number that the first beam is projected onto, is different in different apparatus, the pixel numbers assigned to a specific wavelength in the wavelength calibration table of the different apparatuses will differ. In this case, software may be used to produce a standard set of wavelengths as follows:

(i) Establish a set of wavelengths common to the wavelength calibration table of the different apparatus.
(ii) Select a range of wavelengths of the standard set of wavelengths, the range of wavelengths having wavelengths belonging to the standard set of wavelength.

It should be understood that the wavelength calibration table obtained from different apparatus as described in above third method may be such that a pixel number from different apparatus may not be assigned the same wavelength. It should also be understood that the first pixel may be an approximation to a pixel number and also the first pixels from different apparatus may be approximated to be the same pixel, and that the approximations tolerated depends on the prediction accuracy required for the primary calibration algorithms. In other words, the identification of the first pixel may be incorrect. An incorrect identification can be tolerated provided that the incorrectly identified pixel is within less than or equal to about +/-N pixel, where N is the number of pixels that encompass a range of wavelength. Fore example, if the pixel dispersion is 2 nm and if the tolerated error is +/-10 nm, then the incorrectly identified pixel must be no more than 5 pixels away on either side of the actual pixel on which the beam impinged. Different levels of error may be tolerated typically, but not limited to ±2 nm to ±20 nm and more preferably from ±2 nm to ±10 nm. Selection of a wavelength calibration method depends on the required prediction accuracy of the primary calibration algorithms.

For the purpose of calibration, the actual wavelengths may be irrelevant, if the number of wavelengths in the standard set of wavelength is equal to the number of pixels of the linear diode array, and the pixels in each linear diode array are equivalent (for the required accuracy of the predicted value of an analyte), in terms of wavelength. The identification of the actual wavelengths associated with each pixel is not necessary to generate calibration algorithms. In the examples of primary calibration algorithms for hemoglobin discussed below, the pixel number could be used instead of the actual wavelength. The actual wavelength is required when the wavelength corresponding to a particular pixel in one linear diode array is different from the wavelength corresponding to the same pixel in a different linear diode array. Also, the actual wavelength is useful for identifying analytes with characteristic absorbance peaks. For example, hemoglobin has two characteristic absorbance peaks at 540 nm and 578 nm. These absorbance peaks may be used to identify the hemoglobin signal. If one wavelength is used to perform the wavelength calibration, it is preferred that a wavelength that is close to the primary calibration wavelength of the primary calibration algorithm be used. If more than one wavelength is used, it is preferred that the wavelengths are significant with respect to the analyte signal. For example, a calibration algorithm for hemoglobin would preferably comprise a first beam of about 593 nm to 608 nm, according to the hemoglobin primary calibration algorithm in Example 2.

In the examples described below, the apparatus are used to measure concentrations of interferents in serum and plasma using radiation, most preferably using near infrared radiation and the adjacent visible radiation spectrum, for example, but not limited to, any suitable wavelength from about 300 nm to about 2500 nm, preferably from about 500 nm to about 1100 nm, and more preferably, from about 500 nm to about 800 nm.

B) Primary Calibration

The process of primary calibration is used to develop a primary calibration algorithm for each analyte. Primary calibration of an apparatus is a cumbersome, time intensive exercise because the primary calibration set is relatively large, and the samples in the primary calibration set should be real or very close to real samples. Preferably, samples include all the absorbance variability expected in a sample, whereby the sample variability becomes built into the primary calibration algorithm. It will be obvious to those skilled in the art that sample variability can also be due to inter-apparatus variability, which can also become built into the primary calibration algorithm by including measurements from one or more samples of the primary calibration set measured on one or more than one first apparatus. Vessels also contribute variability, and it is possible to develop one or more primary calibration algorithm using a combination of more than one vessel, whereby the vessel variability may become built into the primary calibration algorithm. However, development of primary calibration algorithms that are specific to a particular type of vessel is preferred.

A primary calibration algorithm can be obtained as follows: Absorbance spectra are obtained for several samples each of which having a different concentration of a given analyte for which the primary calibration algorithm is being developed. It is preferred that the samples include all the absorbance variability expected in a sample, whereby the sample variability becomes built into the primary calibration algorithm. Furthermore, measurements from one or more samples of the primary calibration set on more than one first apparatus may be combined to include variability between apparatus into the calibration algorithm. As a non-limiting example, a step-wise multiple linear regression may then performed to determine at which wavelengths the order derivative of absorbance correlates best with the concentration of the analyte. Then, using multiple linear regression a linear combination having the order derivative of absorbanceat specific (chosen by step-wise linear regression) wavelengths as the independent variable and the concentration of the analyte as the dependent variable is generated. In the step-wise linear regression, an order derivative of absorbance or measurements for all the wavelengths may be presented to the StatView™ program. Only the wavelengths at which the order derivative of absorbance exhibits a correlation coefficient within a predetermined range are selected for the algorithms.

In another embodiment, a smaller set of samples like those of the primary calibration set, or a subset of the primary calibration set, or both, can be measured on a second apparatus, and the data combined with some or all of the original data from the primary calibration set, to develop one, or more than one, upgraded primary calibration algorithm.

Software tools used for developing primary calibration algorithms comprises of the following: Mathlab™ used to create programs for smoothing absorbances and derivative of absorbances. MS Excel™ may be used to develop macros for calculating first and higher order derivative of absorbances; StatView™ used to create algorithms by "step-wise multiple linear regression." Pirouette may be used to create calibration algorithms by Partial Least Squares (PLS) or Principal Component Analysis (PCA), using the measurements for all the wavelengths, or selected sections of the absorbance spectra. It will be appreciated however that other software tools may also be used. It will also be appreciated that any statistical technique may be used for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks. It will also be appreciated that determination of analyte concentration in a sample in a second apparatus may be accomplished by using data pre-processing, including smoothing, calculation of first and higher order derivative of absorbance, interpolation of absorbances, multiplicative scatter correction, or data transformation, prior to primary calibration algorithm development. Photometric correction may also be used on second apparatus depending on the required accuracy of the predicted value of an analyte concentration. Any other methods of primary calibration algorithm development and any form of data transformation are within the scope of this invention. Example of data transformation, which should not be considered limiting in any way, include determining the log and anti-log of the analyte concentration, and Fourier transformation, which are well known to those skilled in the art (Osborne, B. G., Fearn, T & Hindle, P. H., Practical NIR Spectroscopy with Applications in Food and Beverage Analysis, 1993, Published by Longman Scientific & Technical, which is incorporated herein by reference).

Multiplicative scatter correction may also be used, when spectrophotometric data from more that one apparatus is combined. Preferably, the calibration algorithm is applied to the spectrophotometric data of future samples after data pre-processing.

Each apparatus used for the purpose of determining the concentration of analytes in a sample, must be calibrated according to this process on an as needed basis. The primary calibration procedure, in respect of interferents, is set out here. Although it will be appreciated by those skilled in the art that the procedures set out here for interferents will apply to any analyte, in any sample, and a primary calibration algorithm may contain from a single wavelength term, in the simplest case, to multiple terms that use all the wavelengths. Further, any multivariate data analysis technique may be used with any order derivative of absorbance.

Installation of a primary calibration algorithm in a second apparatus can take place at any time, including when the second apparatus is being manufactured, or just prior to use. Preferably, the primary calibration algorithm(s) is/are incorporated into the hardware of a second apparatus, for example, but not limited to, an EPROM that is installed in a second apparatus thereby incorporating the primary calibration algorithm. However, the primary calibration algorithm may also be stored on any other suitable medium, for example, but not limited to a calibration diskette and incorporated in the apparatus as required. The incorporated algorithms are preferably used in the second apparatus after the absorbance measurements are interpolated and mapped onto the same standard set of wavelengths used for the primary calibration and after photometric correction is performed for each relevant wavelength. Preferably, calibrators used for photometric correction are synthetic fluids, but other materials may also be used. More preferably, a calibration package as discussed under the title "Calibration Package" comprising calibrators and at least one primary calibration algorithm may be used. Examples of slopes and intercepts which may be used for photometric corrections are given in Table 1 of Example 1. The wavelengths in Example 1 are from a standard set of wavelengths.

Examples of deriving a primary calibration algorithm for hemoglobin, bilirubin and turbidity are provided below, however, it should be understood that these examples are not to be considered limiting in any manner.

Calibration sets for hemoglobin (Hb), biliverdin (BV), bilirubin (BR) and turbidity in serum are described below. Intralipid™ (IL), a fat emulsion, is used to mimic turbidity. The four analytes mentioned are the major contributors of absorbance variability in serum and plasma samples. Following the description of the calibration sets, are several sample primary calibration algorithms.

Hemoglobin and Biliverdin

To prepare a Primary Calibration Algorithm for hemoglobin, sixty serum specimens with no visible interferents were stored refrigerated or frozen until used. More or fewer specimens may be used so long as a sufficient number is used to provide robust algorithm(s). Hb, IL, BR and BV were added to the normal sera to give final concentrations of 0–6.1 g/L, 0–5.1 g/l, 0–42.7 mg/dL, and 0–4.4 mg/dL respectively. Stock Hb was prepared by replacing the plasma (must be free from all interferents) from a blood sample, with twice its volume of water, and lysing the cells through three freeze-thaw cycles. For each cycle the blood was left in the freezer for 45–60 minutes, and then removed and placed on a rocker at room temperature for 30–45 minutes. Hb content of the lysate was measured by the reference method described below, after removing the red blood cell (RBC) debris and unlysed RBC's by centrifuging at 10,000×g for 10 minutes. Any method which provides a reliable determination of Hb content may be used. A typical hemolysate contains approximately 100 g/L Hb. CO-oximetry suggests that more than 95% of the Hb is in the oxy-Hb state. Stock BV was prepared by dissolving biliverdin dihydrochloride (from Sigma) initially in 50% methanol-50% water, and diluting further with phosphate buffered saline (PBS). Stock IL also known as Travamulsion™ (from Clintec-Nestle & Baxter) has a concentration of 10%. Stock BR was prepared by dissolving Ditauro-Bilirubin (from Porphyrin Products, Logan, Utah, USA) in interferent-free serum, to a concentration of 500 mg/dL. The spectral absorbance data were recorded for the 60 samples using different polypropylene dispensing tips. Out of the 60 samples, odd numbers were used for the calibration set, and even numbers were used as the validation set.

Bilirubin

The sample set used for Hb and BV calibrations are not typically used for BR calibration, because the absorbance due to either Hb >4 g/L or IL >4 g/L, approaches the limit of the apparatus in the region around 524 nm, a primary wavelength used for BR calibration. Instead, a separate set of 60 samples were prepared and tested. As will be readily appreciated by those skilled in the art, the sample set used for primary calibration should be of a size sufficient to include most of the variability encountered with actual patient samples, such as serum or plasma. The samples were prepared as before by adding Hb, IL BR and BV to the normal sera to give final concentrations of 0–2.6 g/L, 0–3.6 g/l, 0–37 mg/dL, and 0–4.4 mg/dL respectively. The spectral absorbance data were recorded for the 60 samples using different polypropylene dispensing tips. Out of the 60 samples, odd numbers were used for the calibration set, and even numbers were used as the validation set. The stock interferents were prepared as described above for Hb, and the BR concentrations were adjusted by the factor 1.23. The 1.23 factor that was derived previously from the slope of the regression line obtained from a validation set using real icteric serum and plasma samples.

Turbidity

Turbidity in serum and plasma is caused mainly by the presence of fat particles, particularly chylomicrons. Intralipid (IL) is a fat emulsion which mimics naturally-occurring chylomicrons, and therefore may preferably be used to simulate turbidity in serum and plasma.

Samples used for Hb and BR calibration are preferably not used for IL calibration because the Hb stock solution contributes significant light scattering due to unlysed red blood cells (RBC's) and RBC fragments. Centrifugation of the hemolysate was unable to remove all the unlysed RBC and RBC fragments.

Forty samples of PBS (phosphate buffered saline) were spiked with 10% Intralipid to produce concentrations of 0–20 g/L. The spectral absorbance data were recorded for the 40 samples using different polypropylene dispensing tips. Out of the 40 samples, the odd numbers were used for the calibration set, and the even numbers were used as the validation set.

As mentioned above, the primary calibration described herein is exemplary of the work involved in developing primary calibration algorithms. Other analytes may be used to develop such primary calibration algorithms.

Primary Calibration Algorithms

The following Primary Calibration Algorithms were developed for Hb, BV, BR and IL (turbidity) in disposable polypropylene dispensing tips using the primary calibration approach set forth above.

Hemoglobin $$\text{g/L Hb}=16.81 \ (1\text{st } D\ A584)-79.47 \ (1\text{st } D\ A599)+60.95 \ (1\text{st } D\ A617)+0.24$$

where (1st D A) is the first derivative of the absorbance measurement at the wavelength specified in nanometers.

Bilirubin $$\text{mg/dL BR}=-293.1 \ (1\text{st } D\ A524)-327.8 \ (1\text{st } D\ A587)+451.7 \ (1\text{st } D\ A602)-7.5$$

where (1st D A) is the first derivative of the absorbance measurement at the wavelength specified in nanometers.

Turbidity

Turbidity is measured in terms of equivalent IL concentration.

$$\ln \ (\text{g/L IL})=1.867(A700)-0.447(A700)^2+0.041(A700)^3-1.33$$

where (A) is the raw absorbance measurement at the wavelength specified in nanometers.

A further set of primary calibration algorithms developed on another apparatus used to test the samples for measurement in disposable polypropylene dispensing tips, are as follows:

Hemoglobin $$\text{(g/L) Hb}=30.14 \ (1\text{st } D\ A591 \text{ nm})-27.98 \ (1\text{st } D\ A610 \text{ nm})$$

where (1st D A) is the first derivative of the absorbance measurement at the wavelength specified.

Bilirubin $$\text{mg/dL BR}=142.09 \ (1\text{st } D\ A511 \text{ nm})+89.9 \ (1\text{st } D\ A554 \text{ nm})-4.47$$

where (1st D A) is the first derivative of the absorbance measurement at the wavelength specified.

Biliverdin $$\text{mg/dL BV}=160.29 \ (1\text{st } D\ A718 \text{ nm})-206.15 \ (1\text{st } D\ A781 \text{ nm})+1.42$$

where (1st D A) is the first derivative of the absorbance measurement at the wavelength specified.

Turbidity $$\text{g/L IL}=296.01 \ (A900 \text{ nm})-0.04$$

where (A) is the raw absorbance measurement at the wavelength specified.

The Primary Calibration Algorithms referred to herein are non-limiting examples obtained by a process of step-wise multiple linear regression. Determination of analyte concentration in a sample in a second apparatus may be accomplished by using an order derivative of absorbance, including zero order, in the primary calibration algorithm, and photometric correction may or may not be necessary, depending on the required accuracy of the predicted analyte concentration. Any statistical technique may be used for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks.

It is noted that in developing a primary calibration algorithm the absorbance and wavelength variabilities acceptable in a batch of apparatus depends on the accuracy requirement for the analyte. Further, the absorbance and wavelength variabilities acceptable in a batch of apparatus depend on the requirement of the inter-apparatus variability of the analyte concentration.

As indicated above, several examples for primary calibration algorithms for the same analyte have been shown. Some reasons why different primary calibration algorithms are generated are as follows: the primary calibration algorithms are generated by different people, using the same software tools; the primary calibration algorithms are generated by the same or different people, using different software tools; wider analytical range is required (e.g., measuring high levels of Hb-based blood substitutes, which give the appearance of high levels of real Hb), as described in WO 9839634 (which is incorporated herein by reference).

The conventional method to deal with a concentration that exceeds the upper limit of the analytical range is to dilute the sample. New wavelengths may be used, and/or new mathematical transformation(s) may be used, instead of diluting the sample. For example, either a cubic primary calibration algorithm that uses natural logs, or a linear single term primary calibration algorithm was shown for turbidity; the cubic primary calibration algorithm was developed for a wider analytical range of turbidity. As another example, greater accuracy may be required at low concentrations of Hb and therefore a calibration algorithm may be developed to measure traces of Hb in serum or plasma over a small analytical range, and when the predicted value exceeds the upper limit of the analytical range, the software could be prompted to use a different calibration algorithm, which covers a wider analytical range. As yet another example, when the wavelength range provided by the apparatus is limited, for example, one apparatus may only have the capability of measuring 450–750 nm, instead of 450–1100 nm, the primary calibration algorithms for IL may use 700 nm and 900 nm respectively.

An important aspect of primary calibration algorithm development is the validation process that is described next. Validation requires a sample set similar to the calibration set; the calibration set cannot be used for validation. Validation may be a test of robustness of the primary calibration algorithms, depending on the overall variability presented in the validation set. If the calibration algorithm for a particular analyte cannot accurately predict the concentration of the analyte in the sample, it could be that the variability in the test sample was not included in the primary calibration set. In other words, the primary calibration algorithm for the analyte lacked robustness. Robustness can also be added by combining the measurements of one or more of the primary calibration set obtained from the first apparatus and one or more similar apparatus.

C) Validation

Hemoglobin and Biliverdin

As mentioned above in the section on primary calibration, out of the 60 samples, odd numbers were used for the primary calibration set, and even numbers were used as the validation set.

Bilirubin

As mentioned above in the section on primary calibration, out of the 60 samples, odd numbers were used for the primary calibration set, and even numbers were used as the validation set.

Turbidity

As mentioned above in the section on primary calibration, out of the 40 samples, the odd numbers were used for the primary calibration set, and the even numbers were used as the validation set.

An important requirement of validation is the availability of a reliable reference method for a particular analyte. A reference method is required to determine the actual or true concentration of the analyte in the sample. The difference in the true concentration, as measured by the reference method, and the concentration predicted by the primary calibration algorithm, is a measure of prediction accuracy of the primary calibration algorithm. The next section describes some reference methods.

Reference Methods

The sample absorbance data and the concentrations of the interferents are required for development of calibration algorithms for the interferents. Any errors in the reference methods used to measure the concentration of the interferents will affect the prediction accuracy of the primary calibration algorithms.

Hemoglobin

For validation using spiked serum samples, the Hb concentration in the hemolysate was used to calculate the reference Hb values. For validation using serum or plasma samples, methods known to those skilled in the art, such as for example: Tietz Textbook of Clinical Chemistry, 1994, page 2024, may be used; the same method is used to determine the Hb concentration in the hemolysate.

For accurate hemoglobin measurement in serum and plasma samples, preferably they will be the only analyte present, and the absorbances at 578 nm, 562 nm, and 598 nm may be measured and the concentration of hemoglobin determined using the following equation:

$$\text{mg/dL Oxy-hemoglobin} = 155.0\, A_{578} - 86.1\, A_{562} - 68.9\, A_{598}$$

where: A is the absorbance at the wavelengths specified in nanometers. Appropriate dilutions are performed to produce absorbances between 1.0 and 2.0, for the 578 nm wavelength.

As appropriate, dilutions may be made with 10 mg/dL sodium carbonate. Any other reliable reference method may be used. For the present illustration of primary calibration, a Shimadzu single-beam scanning spectrometer with a grating was used, although any comparable apparatus may be used.

Biliverdin

The weighed amount of added biliverdin dihydrochloride was used instead of an actual method for measuring the concentration of BV in the samples.

Bilirubin

For validation using spiked serum samples, the concentration of synthetic ditauro-bilirubin added, divided by 1.23, was used as the reference total BR value. For validation using patient serum or plasma samples, any total bilirubin test performed by chemistry analyzers (e.g., Beckman-Coulter or Ortho-Clinical Diagnostics general chemistry analyzers) used by accredited medical laboratories could be used as the reference method.

As mentioned before, the 1.23 factor used was derived previously from the slope of the regression line obtained from a validation set using real icteric serum and plasma samples.

Turbidity

For validation using PBS spiked with IL, the concentration of the IL present was used as the reference value. In Tietz Textbook of Clinical Chemistry, 1994, page 2022, absorbance measurement at 700 nm is used to make corrections for turbidity. Therefore, for this instance, validation using patient serum or plasma samples, absolute absorbance at 700 nm may be adopted as the reference method. A commercial single beam spectrophotometer should be used with a 10 mm×10 mm cuvette, referenced against PBS. The absorbances before or after dilutions should preferably be between 0.2 and 2.0. Photometric and wavelength accuracy of the reference spectrophotometer should preferably be demonstrated before use.

D) Calibration Algorithm Transfer

The present invention provides a method for transferring a calibration algorithm from a first apparatus to a second apparatus whereby the second apparatus need not be calibrated in the same way in which the first apparatus was calibrated, that is by conducting a primary calibration.

According to one embodiment the present invention provides a method for calibration algorithm transfer from a first apparatus to a second apparatus comprising:

(i) obtaining a first set of absorbance measurements of a set of calibrators on a First Apparatus that is in control at wavelengths from a first wavelength calibration table;

(ii) establishing a second wavelength calibration table on a second apparatus, the first and the second wavelength calibration table may be the same or different, and obtaining a second set of absorbance measurements of the set of calibrators on the Second Apparatus, at wavelengths from the second wavelength calibration table;

(iii) determining a first interpolated absorbance for the first absorbance measurements for at least one wavelength of a Standard Set of Wavelengths, and determining a second interpolated absorbance for the second absorbance measurements for the at least one wavelength of the Standard Set of Wavelengths, (iv) deriving a First Linear Regression Equation for each of the at least one wavelength of the Standard Set of Wavelengths using the first and the second interpolated absorbance measurement;

(v) incorporating the First Linear Regression Equation and at least one Primary Calibration Algorithm onto the Second Apparatus.

Subsequent to calibration algorithm transfer, according to an embodiment of the invention, there is further provided a method of determining the concentration of an analyte in a sample in a second apparatus comprising:

(a) performing a Calibration Algorithm Transfer according to the method described above;

(b) measuring an absorbance of the sample on the second apparatus, and determining a sample interpolated absorbance for at least one wavelength of the Standard Set of wavelengths;

(c) adjusting the interpolated absorbance with the First Linear Regression Equation to obtain an Adjusted Interpolated Absorbance; and (d) calculating a concentration for the analyte by applying the at least one Primary Calibration Algorithm for the analyte to the Adjusted Interpolated Absorbance.

It should be understood that not all of the steps described above are required, and that some of the steps described above are optional.

The first linear regression equation is derived from a plot of interpolated absorbance measurements, the first interpolated absorbance measurements preferably on an x-axis, the second interpolated absorbance measurements preferably on a y-axis, and the first linear regression equation having a y-intercept and a slope. It should be understood that the first interpolated absorbances may be plotted on the y-axis and the second interpolated absorbances plotted on the x-axis. In such case, Adjusted Interpolated Absorbance=(Slope× Interpolated Absorbance)+Y-intercept. By interpolated absorbance, it is meant the absorbance value for a specific wavelength of the standard set of wavelengths. If the specific wavelength of the standard set of wavelengths is the same as the wavelength already assigned to a pixel of a linear diode array, then the interpolated absorbance is the same as the measured absorbance. However, if the specific wavelength is different from the wavelength assigned to a pixel, then the value of interpolated absorbance, at the specific wavelength, is estimated from the measured absorbance values of at least two adjacent pixels whose wavelengths encompass one or more standard wavelengths.

Examples of first linear regression equations are shown in Example 1. This adjustment of absorbance is also referred to as photometric correction. Accordingly, the measurement made in respect of the sample once adjusted provides a result comparable to that which would be obtained if the sample had been measured on the first apparatus. In this way, the second apparatus need not be calibrated through primary calibration as was done for the first apparatus.

According to a preferred embodiment the primary calibration algorithms and the interpolated absorbance measurements of the calibrators made on the first apparatus are electronically stored and installed on the second apparatus. Electronic storage includes more preferably a floppy diskette or CD. More preferably, a calibration package as discussed under the title "Calibration Package" comprising of calibrators and at least one primary calibration algorithm may be used.

It is also preferred that the samples used for the Primary Calibration, and the calibrators, are placed within like vessels having optical properties substantially similar. Non-limiting examples of vessels that can be used are, a pipette tip, a labeled test tube, an unlabeled test tube, a blood bag tubing, any transparent container, or any translucent container. In one aspect of the invention the sample can be liquid for example, a biological fluid, including but not limited to bodily fluids for example serum or plasma, or non-biological, for example but not limited to a beverage or a synthetic calibrator, or solid for example cheese, which is not to be considered limiting in any manner, or a medicament, for example a pharmaceutical tablet. In another aspect of the invention, a sample exhibits one or more properties that may be determined spectrophotometrically. A sample typically comprises one or more analytes. By analyte it is meant a substance being measured in a sample. A sample is characterized in that the energy of one or more wavelengths of light can be either transmitted, absorbed, scattered, reflected, or a combination thereof, by an analyte within the sample. The light that is measured in the preferred embodiment is the transmitted light, and the transmitted light is converted into absorbance units. It should be understood that the absorbance units are not true absorbance units, as would be obvious by those skilled in the art.

In another aspect of the invention, a set of calibrators are defined as two or more calibrators and the set of calibrators and the sample are placed within a like vessel used for the primary calibration. Furthermore, any type of calibrator suitable for producing a set of first linear regression equations based on interpolated absorbances obtained using a first apparatus and a second apparatus, may be used. For example, a set of calibrators may comprise translucent substances such as fiberglass which may vary in thickness, color, or finish, depending on the type of analyte to be measured. The calibrators may also comprise solid particles in liquid suspension, e.g., polystyrene beads in a buffer of similar density as the polystyrene beads. Calibrators may also comprise fat emulsion, for example fat particles in suspension. Calibrators may also comprise colored glass of varying thickness and finish. In any event, the calibrators should produce a suitable set of first linear regression equations on a First Apparatus and a Second Apparatus based on interpolated absorbances on the respective apparatus. In the preferred embodiment, the set of calibrators tested on both first apparatus and second apparatus, are from the same batch. Further, the calibrators used on the second apparatus may be the same as the set of calibrators used on the first apparatus.

In another aspect of the invention, a standard set of wavelengths comprise wavelengths from about 300 nm to about 2500 nm, preferably from about 500 nm to about 1100 nm, and more preferably, from about 500 nm to about 800 nm.

In another aspect of the invention, the first and the second absorbance measurements are determined one or more times at each wavelength of a calibration table, and an average of the first, or the second, interpolated absorbance(s) is mapped to the standard set of wavelengths. Further, the standard set of wavelengths used by both the first apparatus and the second apparatus are the same.

According to one embodiment of the invention, a standard set of wavelengths is a set of wavelengths used by all apparatus in conjunction with the apparatus-specific wavelength calibration table, used to generate interpolated absorbances from the actual absorbances. More details are provided in the section entitled "Wavelength Calibration." The actual absorbances of a sample tested on an apparatus are measured at wavelengths from the wavelength calibration table, and these actual absorbances are interpolated and mapped onto the standard set of wavelengths. The primary calibration algorithm(s) is/are preferably applied to the interpolated mapped absorbances—not the actual absorbances. Without wishing to be limiting in any manner, an example of a standard set of wavelengths includes 500 to 1100 nm, in increments of 2 nm, i.e., a pixeldispersion of 2 nm. However, other wavelength ranges and pixeldispersions may be used as required, and as would be known by one of skill in the art. Spectrophotometers may be designed to have the same wavelength calibration table by projecting a single beam of known wavelength on the same pixel in each linear diode array, and extrapolating to obtain the wavelengths corresponding to the other pixels using the same pixeldispersion. When all apparatus use the same wavelength calibration table, such that the wavelength calibration table becomes the standard set of wavelengths, the step of interpolating absorbances is automatically eliminated. As previously mentioned, pixeldispersion means the wavelengths encompassed by two adjacent pixels of a linear diode array, usually measured in nanometers (nm) per pixel. For example, if two lasers of 600 nm and 900 nm are used for wavelength calibration, and they are projected on pixel 20 and pixel 220 respectively, that means 300 nm (i.e., 900–600 nm) are encompassed by 200 pixels (i.e., 220-20 pixels). Therefore the pixeldispersion is calculated to be 1.5 nm per pixel (i.e., 300 nm divided by 200 pixels).

According to one aspect of the invention, the pixeldispersion may be predetermined by the steps comprising:

(i) Projecting an electromagnetic radiation of known wavelength, onto a first pixel preferably towards an end of a linear diode array;

(ii) Using a second electromagnetic radiation of a known wavelength, projecting the second laser or second light onto a second pixel preferably at the opposite end of the linear diode array;

(iii) Identifying the first and second pixels within the linear diode array; and (iv) Calculating the pixeldispersion in nanometers per pixel or any wavelength units per pixel as described above.

In one aspect of the invention, the pixeldispersion may be calculated in step (iv) for one linear diode array and may be used as the predetermined pixeldispersion. In another aspect of the invention, steps (i) to (iv) may be repeated on one or more apparatus, preferably, the apparatus have similar linear diode arrays, and the average pixeldispersion may be used as the predetermined pixeldispersion. It is understood that the predetermined pixeldispersion may be provided by the manufacturer of the spectrophotometer.

The wavelength calibration table may be obtained by:

(i) projecting a first electromagnetic radiation of known wavelength, onto a first pixel of a first linear diode array of the first apparatus, or a second linear diode array of the second apparatus;

(ii) using a second electromagnetic radiation of known wavelength, the second electromagnetic radiation having a different wavelength than the first electromagnetic radiation, projecting the second electromagnetic radiation onto a second pixel of the first or the second linear diode array;

(iii) identifying the first and second pixels within the first or the second linear diode array;

(iv) calculating a pixeldispersion for the first or the second linear diode array; and (v) assigning a wavelength to each pixel within the first or the second linear diode array to produce the wavelength calibration table using the pixeldispersion and either the first electromagnetic radiation of known wavelength, and the first pixel, or the second electromagnetic radiation of known wavelength and the second pixel.

In another aspect of the invention, the wavelength calibration table is obtained by projecting only the first electromagnetic radiation of known wavelength onto an identified first pixel of the linear diode array, using a predetermined pixeldispersion. Further, according to this method using a only a first beam, wherein the method is repeated on a second apparatus, preferably with similar components, the wavelength calibration table of the second apparatus is determined using the same pixel number of the first pixel. Therefore, the wavelength calibration table could be the standard set of wavelengths.

In a further aspect, the wavelength calibration table of the second apparatus may be determined by projecting only a first beam on a pixel of a different pixel number as that of the first apparatus.

In a preferred embodiment where analyte accuracy is critical, two wavelengths should be used to facilitate determination of the pixeldispersion for the apparatus, and a specific wavelength calibration table is generated for each apparatus using the two wavelengths, their corresponding pixel numbers, and the calculated pixeldispersion. In another embodiment where analyte acuracy is not as critical, a single wavelength, its corresponding pixel number, and a predetermined pixeldispersion should be used to generate a wavelength calibration table. It is understood that if the single wavelength is projected onto the same pixel number of like linear diode arrays in different apparatus, the same wavelength calibration table would be generated. It is also understood that if the same wavelength calibration table is generated, the wavelength calibration table becomes the standard set of wavelengths, thereby eliminating the step of wavelength interpolation and mapping. It is also understood that if the wavelength calibration table is the same for each apparatus, pixel numbers can be used in the primary calibration algorithm(s) instead of wavelengths. Example 6 illustrates the resulting wavelength inaccuracy when the beam does not project on the same pixel number in every linear diode array. It is obvious to those skilled in the art that wavelength inaccuracy is translated into absorbance inaccuracy.

E) Recalibration

The present invention provides a method for recalibrating an apparatus that was previously calibrated by calibration algorithm transfer, but is no longer in control, comprising the following steps:

(i) obtaining absorbance measurements of a set of calibrators on the apparatus, the set of calibrators having assigned absorbance values, the apparatus comprising a Primary Calibration Algorithm;

(ii) determining interpolated absorbance values for the absorbance measurements for at least one wavelength of a Standard Set of Wavelengths;

(iii) establishing a Second Linear Regression Equation in the apparatus, using the interpolated absorbance values and the assigned absorbance values; and (iv) incorporating the Second Linear Regression Equation on the apparatus to produce a recalibrated apparatus.

Subsequent to recalibration, according to an embodiment of the invention, there is further provided a method of determining the concentration of an analyte in a sample in a Second Apparatus comprising the following steps:

(a) recalibrating the apparatus according to the method described above;

(b) measuring an absorbance measurement of the sample;

(c) deriving an interpolated absorbance for the absorbance measurement for at least one wavelength of the Standard Set of Wavelengths in the recalibrated apparatus;

(d) adjusting the interpolated absorbance measurement with the Second Linear Regression Equation to obtain an Adjusted Interpolated Absorbance; and (e) calculating a concentration for the analyte by applying the Primary Calibration Algorithm for the analyte to the Adjusted Interpolated Absorbance.

It should be understood that not all of the above step are required, and that some of the steps described above are optional.

It is also understood that the definition of terms used in recalibration are as described at the beginning of "Detailed Description of Invention." Further, it should be understood that recalibration is a sequel to calibration algorithm transfer, when an apparatus is no longer in control.

Second linear regression equations are developed for each relevant wavelength of a standard set of wavelengths, with the interpolated absorbance measurements from the Set of calibrators versus absorbance measurements assigned to the lot or batch of calibrators, after the absorbances of the calibrators were measured on the first apparatus when it was in control. The second linear regression equation is derived from a plot of the absorbance measurements of the calibrators, preferably with the interpolated absorbance from the second apparatus on a y-axis and the assigned absorbance from the first apparatus on an x-axis. Each generated second linear regression equation having an intercept and slope, is then stored electronically in the apparatus being recalibrated. Electronic storage includes more preferably a floppy diskette or CD. Accordingly, the interpolated absorbance in respect of the sample once adjusted, provides a result comparable to that which would be obtained if the sample had been measured on the first apparatus. In this way, the second apparatus need not be calibrated through a primary calibration as was done for the first apparatus.

For clarity, the term "Second Linear Regression" was used for recalibration (and also for calibration as will be seen under the title "Calibration") of an apparatus and the term "First Linear Regression" was used for calibration algorithm transfer. According to an aspect of the invention, when compared to calibration algorithm transfer the only new requirement in the process of recalibration of an apparatus is determination of interpolated absorbances of two or more calibrators for at least one wavelength of a standard set of wavelengths on the apparatus. Further, the first apparatus is not required, because recalibration is a sequel to calibration algorithm transfer, and therefore the primary calibration algorithm(s) is, or are, already incorporated in the second apparatus.

F) Calibration

Calibration is the process of establishing and incorporating one or more second linear regression equations in an apparatus that was never subjected to calibration algorithm transfer. Therefore the primary calibration algorithm(s) is or are yet to be incorporated in the apparatus. Like recalibration, calibration does not require the first apparatus. A method for calibrating an apparatus that was never subjected to calibration algorithm transfer, comprises the following:

(i) obtaining absorbance measurements of a Set of Calibrators on the apparatus, the apparatus lacking a primary calibration algorithm, and the set of calibrators having assigned absorbance values, (ii) determining interpolated absorbance values for the absorbance measurements for at least one wavelength of a Standard Set of Wavelengths;

(iii) establishing a Second Linear Regression Equation in the apparatus, using the interpolated absorbance measurements and the assigned absorbance values; and (iv) incorporating the Second Linear Regression Equation, and at least one Primary Calibration Algorithm on the apparatus, to produce a calibrated apparatus.

Subsequent to calibration, according to an embodiment of the invention, there is further provided a method of determining the concentration of an analyte in a sample in a calibrated apparatus comprising:

(a) calibrating the apparatus according to the method described above;

(b) measuring an absorbance value of the sample;

(c) deriving an interpolated absorbance from the absorbance value for at least one wavelength of the Standard Set of Wavelengths in the calibrated apparatus;

(d) adjusting the interpolated absorbance measurement with the Second Linear Regression Equation to obtain an Adjusted Interpolated Absorbance; and (e) calculating a concentration for the analyte by applying the Primary Calibration Algorithm for the analyte to the Adjusted Interpolated Absorbance.

It should be understood from the definitions of terms used in "Calibration" are as described at the beginning of "Detailed Description of Invention." Further, it should be understood that calibration is for an apparatus that does not have any relevant primary calibration algorithm incorporated in the apparatus.

The essential components of a calibration package (discussed under the title "Calibration Package") comprises of:

i) At least one primary calibration algorithm;

ii) At least two calibrators; and iii) Assigned absorbances for the calibrators.

The assigned absorbances for calibrators are preferably obtained from the first apparatus when the apparatus is in control. By definition of first apparatus, the primary calibration algorithm(s) is/are developed for the first apparatus. Therefore, the assigned absorbances of calibrators and the primary calibration algorithm(s) should preferably originate from the same apparatus. During recalibration, if the calibrators' assigned absorbances do not originate from the same apparatus from which the primary calibration algorithm(s) originated, there exists a risk of having a mismatch between the calibrators' assigned absorbances and the primary calibration algorithm(s). In order to mitigate this risk, it is preferred that the appropriate primary calibration algorithm(s) be reincorporated in the apparatus. It becomes obvious that this preferred form of recalibration is no different from the process of calibration. Therefore, in the preferred embodiment, calibration is a safer approach than recalibration. In other words, calibration is preferred to recalibration when a calibration package is available.

G) Calibration of a Second Apparatus Optionally Using Data Pre-Processing

The inventor has also found that the process of determination of analyte concentration in a sample may be accomplished by using an order derivative of the absorbance, including zero order, optionally combined with other forms of data pre-processing. Photometric correction may or may not be necessary, depending on the required accuracy of the predicted analyte concentration. Any statistical technique may be used to derive the primary calibration algorithm, for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks. Examples of data pre-processing which should not be considered limiting in any way, include smoothing, deriving a first and higher order derivative of absorbance, interpolation of absorbance, multiplicative scatter correction, photometric correction, and data transformation, for example Fourier transformation. Preferably, the calibration algorithm is applied to the absorbance data of future samples after data pre-processing. In a preferred embodiment, the form or combination of forms of data pre-processing used should be the same as used prior to primary calibration algorithm development.

As an example, where an order derivative of absorbance is used, photometric correction may or may not be necessary, provided that the order of derivative of absorbance used in the primary calibration algorithm at the selected wavelength (s) does not contain significant inter-apparatus variability, although the interpolated absorbances of the same sample for at least one of a standard set of wavelengths may contain significant variability. It is well known that absorbance variability can be removed in certain sections of the absorbance spectra, by using an order of derivative of the absorbance. The acceptable variability in the derivative of the absorbance(s) at the wavelength(s) chosen for the calibration depends upon the inter-apparatus variability in the predicted value of the analyte. Smoothing, data transformation, and obtaining higher than zero order absorbance are non-limiting examples of data pre-processing. Another method of data pre-processing is Multiplicative Scatter Correction, which can minimize absorbance variability. Data pre-processing can be included in the statistical technique used to develop primary calibration algorithms. Data preprocessing may also facilitate calibration algorithm transfer with or without the use of photometric correction. Multiplicative scatter correction may also be used, when spectrophotometric data from more that one apparatus is combined.

According to the approach of using an order derivative of absorbance, while the first derivative of absorbance removes most variability between a first and second apparatus, higher derivatives, while still useful and within the scope of the present invention, tend to introduce sharper peaks and accordingly are not as preferred as the first derivatives. Derivatives of absorbance beyond the $2^{nd}$ increase the complexity of the spectra and magnify the noise i.e., the signal to noise ratio decreases. Because the peaks are sharper with the higher order of derivatives, wavelength accuracy becomes more critical for accurate determination of analyte concentration. Multivariate data analysis can be also be used to remove most variability between a first and second apparatus, and therefore the use of zero order derivative of absorbance is within the scope of this invention. The actual order derivative of absorbance and the statistical technique used, with the options of photometric correction and other forms of data pre-processing, depends on the required accuracy of the predicted value of the analyte.

As the requirement of analyte prediction accuracy increases, and as the complexity of the calibration algorithm increases, the need for photometric correction increases. Also, wavelength accuracy requirement depends on the required accuracy of the analyte. For example, attempts can be made to make the instruments with the same wavelength calibration table, thereby eliminating the need for interpolating and mapping absorbances to a standard set of wavelengths. Methods that may be used to generate a standard set of wavelengths are discussed in details elsewhere, for example, in the section on "Wavelength Calibration."

Wavelength accuracy is still critical for efficient calibration algorithm transfer, when the derivatives of absorbance are used, without performing photometric adjustments. To illustrate this point, wavelength inaccuracies were added to the first and second derivative of absorbance obtained from a second apparatus by shifting the first and second derivative of absorbance data to the right by two pixels (2 columns). The effect of doing this may be seen in FIG. 17 and FIG. 18 for the second and first derivative respectively. The offsets are obvious due to the wavelength inaccuracy in the second apparatus. These offsets can be minimized by interpolating and mapping the absorbances to a standard set of wavelengths as described above, without performing photometric adjustments. Further improvement will be seen if the wavelength calibration of each spectrometer is performed with two wavelengths, preferably provided by lasers as opposed to filters, and preferably narrow band-pass filters if filters are used.

Methods disclosed herein and used for spectrophotometer wavelength calibration, the use of a standard set of wavelength, and the use of photometric adjustment using synthetic calibrators, all contribute to efficient calibration algorithm transfer. Proper wavelength calibration requires skill and time. One may choose the best method for spectrophotometer wavelength calibration and omit the photometric adjustment. Alternatively, one may compromise on the wavelength calibration and convert the absorbances measured to absorbances at a standard set of wavelengths, followed by photometric adjustment. Photometric adjustment could be easily implemented by software, following testing of at least two synthetic calibrators. The methods applied to transfer calibration algorithms depend on the required accuracy of the predicted value of the analytes. Note that the accuracy referred to here means closeness to the predictions by a first apparatus.

As mentioned, an aspect of calibration without photometric correction (depending on the required accuracy of the predicted value of the analytes) is the selection of specific wavelengths, i.e., wavelength optimization.

For multiple linear regression, a method used to select wavelengths that show minimum variability in the absorbance, or first derivative of absorbance (or any derivative of absorbance) is to test the primary calibration samples on several apparatus that have the expected amount of absorbance and wavelength variability, and use the data from all the apparatus in the primary calibration set. After the wavelength(s) is/are selected, only the data generated from a first apparatus should be used to develop the primary calibration equation, using the predetermined wavelength (s).

According to one aspect of the invention, a method of determining the concentration of an analyte in a sample in a second apparatus comprises the following:

(i) incorporating at least one primary calibration algorithm that uses an order derivative of absorbance obtained for at least one wavelength of a standard set of wavelengths, on the second apparatus;

(ii) measuring absorbance values of the sample at one or more than one wavelength from a wavelength calibration table on the second apparatus;

(iii) determining interpolated absorbance values from the absorbance values for wavelengths from a standard set of wavelengths;

(iv) obtaining an order derivative of the interpolated absorbance values, using the order of derivative; and (v) calculating a concentration of the Analyte in the sample, by applying the Primary Calibration Algorithm to the derivative.

It should be understood that not all of the above steps are required, and that some of the steps above are optional, depending on the required accuracy of the predicted value of the analytes In the case where the wavelengths of the standard set of wavelengths are the same as wavelengths of the wavelength calibration table, one or more that one wavelength are used in the step of measuring (step (ii)) since this is sufficient to determine the derivative.

In the above method the derivative can of a first, second, or third order. Also the primary calibration algorithm may comprise 1, 2, 3, or 4 wavelengths. The use of zero order derivative of absorbance and one or more than one wavelength, using simple linear regression in the case of one wavelength, or multivariate data analysis in the case of more than one wavelength, is also within the scope of this invention.

In another aspect of the invention, the at least one wavelength is optimized and derived from at least two or more apparatus. Optimization comprises visual examination of the derivative of absorbance spectra, and choosing wavelength(s) that exhibits changes in the derivative absorbance as a function of analyte concentration and which also exhibits a low variability in the derivative of absorbance between apparatus for a given analyte concentration for each relevant wavelength.

In another aspect of the invention, optimization comprises including absorbance and wavelength variability of more than one apparatus as follows:

(i) Obtaining a first set of interpolated absorbance measurement of the same primary calibration samples from the first apparatus and one or more second apparatus; and (ii) Including all the interpolated absorbance measurements (step (i)) in the primary calibration set to select the optimal wavelength(s) to be used to develop the primary calibration algorithm, by the process of stepwise multiple linear regression.

One, or more than one, of the primary calibration set may be measured on the first apparatus and one, or more than one, similar apparatus, in order to develop a robust calibration algorithm(s) that also includes inter-apparatus variability. Such a calibration algorithm would be developed using a combination of measurements obtained from the first apparatus, and one, or more than one, similar apparatus. However, it is preferred that only data from the First Apparatus is used to develop the primary calibration algorithm at the optimized wavelength(s).

Photometric correction or absorbance adjustment of the interpolated absorbance may or may not be required.

H) Synthetic Calibration Fluids

Different primary calibration algorithms should be developed for an analyte in any one type of vessel, including, for example, labeled tube, unlabeled tube, pipette tip, tubing, translucent container or transparent container. Also, a calibration algorithm for an analyte may be developed for a combination of several different types of vessels. As is clear the calibrators will be measured in a first apparatus with the calibrator in a vessel. According to a preferred embodiment of the method of the invention, measurements of the calibrators in a second apparatus are conducted with the calibrators in the same type of container as used for the first apparatus.

A further aspect of consideration with respect to calibrators is that the calibrator used for measurements in the first apparatus and the second apparatus be from the same batch. In a preferred embodiment, a large batch of calibrators is prepared so that there will be a significant period of time before the batch expires or is depleted. In any event, at some time a new batch of calibrators will be required and that time it is preferable that a further primary calibration be conducted. This primary calibration may be conducted on the same first apparatus as used in respect of the first batch of calibrators or a different first apparatus may be used. In addition, different calibrators may be chosen and the batch may therefore include different calibrators. Once the new batch of calibrators is chosen and prepared, the primary calibration as described above is conducted in respect of the first apparatus and as described above, absorbance measurements of the synthetic calibrators are taken, and this information is provided in the calibration package which will be used for calibration and recalibration of apparatus.

The methods just described generally require the use of a first apparatus or a new primary calibration. However, it is also possible to assign absorbance values to a new batch of calibrators without the use of the first apparatus that is in control, and without conducting a cumbersome primary calibration. Alternative solutions to preparing a second batch or lot of calibrators are described under the title "Assigning Absorbances to a second Batch of Calibrators."

The use of such calibrators is preferred to primary calibration because of the following: a much smaller number of synthetic calibrators is required; synthetic calibrators are ready to use—materials for a primary calibration may not always be so readily available and cannot be stored for more than one day; synthetic calibrators are stable at room temperature and have a long shelf life. The materials used in a primary calibration do not have either of these attributes. Primary calibration algorithms require a skilled user, and are usually developed off-line. Finally, with a calibration package, synthetic calibrators are relatively easy to use.

A preferred formulation of calibrators used in Example 1 is a combination of amaranth, phenol red, copper sulfate, and toluidine blue O, in 100 millimoles per liter acetate buffer, pH 3 to 4.

I) Assigning Absorbances to a Second Batch of Calibrators

According to another aspect of the invention where the calibrators are synthetic fluids, there are provided methods for assigning absorbances to the calibrators from new lots or batches, before or after the old lot or batch expires. Accordingly, the present invention provides methods for assigning absorbance values to a second batch of synthetic calibrators on an apparatus comprising:

1) A method for assigning absorbance values to sets of synthetic calibration fluids from a second batch on a first apparatus, comprising:

(i) Testing whether the first apparatus is in control;

(ii) If the test in step (i) is positive, then obtaining the absorbances measured on the first apparatus for at least one wavelength of the standard set of wavelengths, using at least one set of calibrators from the second batch; and (iii) Assigning the mapped absorbances obtained in step (ii) to sets of calibrators from the second batch.

2) A method for assigning absorbance values to sets of a second batch of calibrators on a Second Apparatus having a previously established first set of first linear regression equations for absorbance measurements using sets of calibrators from a first batch, comprising:

(i) Testing whether the Second Apparatus is in control;

(ii) If the test in step (i) is positive, then
  (a) retaining the previously established first set of first linear regression equations;

(iii) Obtaining absorbance measurements on the second apparatus for at least one wavelength of the standard set of wavelengths, using at least one set of calibrators from the second batch;

(iv) Adjusting the mapped absorbances obtained in step (iii) for the at least one set of calibrators from the second batch using the retained, previously established first set of First linear regression equations from step (ii)(a); and (v) Assigning the adjusted absorbances in step (iv) to sets of calibrators from the second batch.

3) A method for assigning absorbance values to sets of a second batch of calibrators on an apparatus having a previously established first set of first linear regression equations for absorbance measurements using sets of calibrators from a first batch, comprising:

(i) Testing whether the apparatus is in control;

(ii) If the test in step (i) is negative, then
  (a) obtaining absorbance measurements on the apparatus for at least one wavelength of the standard set of wavelengths, using at least one set of calibrators from the first batch, and
  (b) establishing a second set of first linear regression equations for the mapped absorbances obtained in step (ii)(a);

(iii) Obtaining absorbance measurements on the Apparatus for at least one wavelength of the Standard Set of Wavelengths, using at least one set of calibrators from the second batch;

(iv) Adjusting the mapped absorbances obtained in step (iii) for the at least one set of calibrators from the second batch using the retained, previously established set of first linear regression equations from step (ii)(a); and (v) Assigning the adjusted absorbances in step (iv) to sets of calibrators from the second batch.

J) Calibration Package

The essential components of a Calibration Package comprises of:

(i) At least one primary calibration algorithm;

(ii) At least two calibrators; and (iii) Assigned absorbances for the calibrators.

The assigned absorbances for calibrators are preferably obtained from the first apparatus when the apparatus is in control. By definition of first apparatus, the primary calibration algorithm(s) is or are developed for the first apparatus. Therefore, the assigned absorbances of calibrators and the primary calibration algorithm(s) should preferably originate from the same apparatus. During recalibration, if the calibrators' assigned absorbances do not originate from the same apparatus from which the primary calibration algorithm(s) originated, there exists a risk of having a mismatch between the calibrators' assigned absorbances and the primary calibration algorithm(s). In order to mitigate this risk, it is preferred that the appropriate primary calibration algorithm(s) be reincorporated in the apparatus. It becomes obvious that this preferred form of recalibration is no different from the process of calibration. Therefore, in the preferred embodiment, calibration is a safer approach than recalibration. In other words, calibration is preferred to recalibration when a calibration package is available.

Other software may be designed to prepare the software component of calibration packages, although any other means by which the primary calibration algorithms and assigned absorbances of calibrators (tested on the same first apparatus used to generate the primary calibration algorithm when the first apparatus is in control) may be transferred are within the scope of the present invention. In one embodiment of the invention, the at least one primary calibration algorithm and the assigned absorbances of calibrators are stored on a diskette although any other means of information transfer is contemplated, including CD-ROM, e-mail, internet information packages. These approaches will carry the assigned absorbances of the calibrations and also carry the primary calibration algorithm(s) from the first apparatus to the second apparatus. Preferably, calibration packages should contain calibrators, to enable users to calibrate other apparatus when necessary, with minimum effort.

A calibration package will most preferably contain the following pieces of information: the identity or the serial number of the first apparatus (i.e., the apparatus used to develop the primary calibration algorithms); the calibration algorithms and the corresponding analyte for each, developed on the first apparatus; the vessel used for primary calibration and used for assigning absorbances to the calibrators using the first apparatus must be checked from a list of sample containers e.g., tips, tubes, tubing; the lot number of the calibration set; the assigned absorbance values for each calibrator, at all the relevant wavelengths; the analytes for which each calibrator from a set may be applied. In a preferred embodiment, each calibrator is tested 10 times and the average of 10 measurements for each wavelength may be used, instead of a single measurement.

Although the description uses interferents as an example, it is obvious that the invention can be applied to other analytes in other samples. Also, although synthetic calibrators are used as examples, it should be understood that other calibrators may be used with this invention.

The following non-limiting examples are illustrative of the present invention:

EXAMPLES

Example 1

Figure 2:
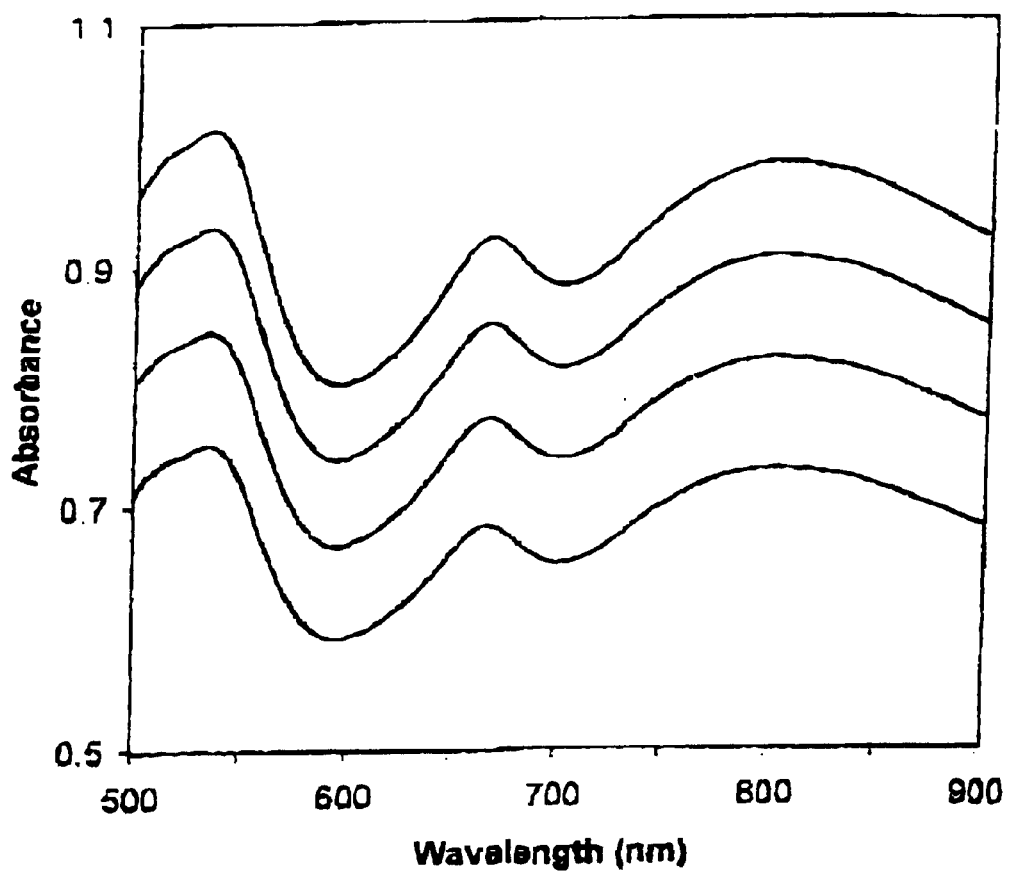
FIG. 2 is a graphic representation of the absorbance spectra of four different synthetic calibrators, tested on the Second Apparatus.
Figure 3:
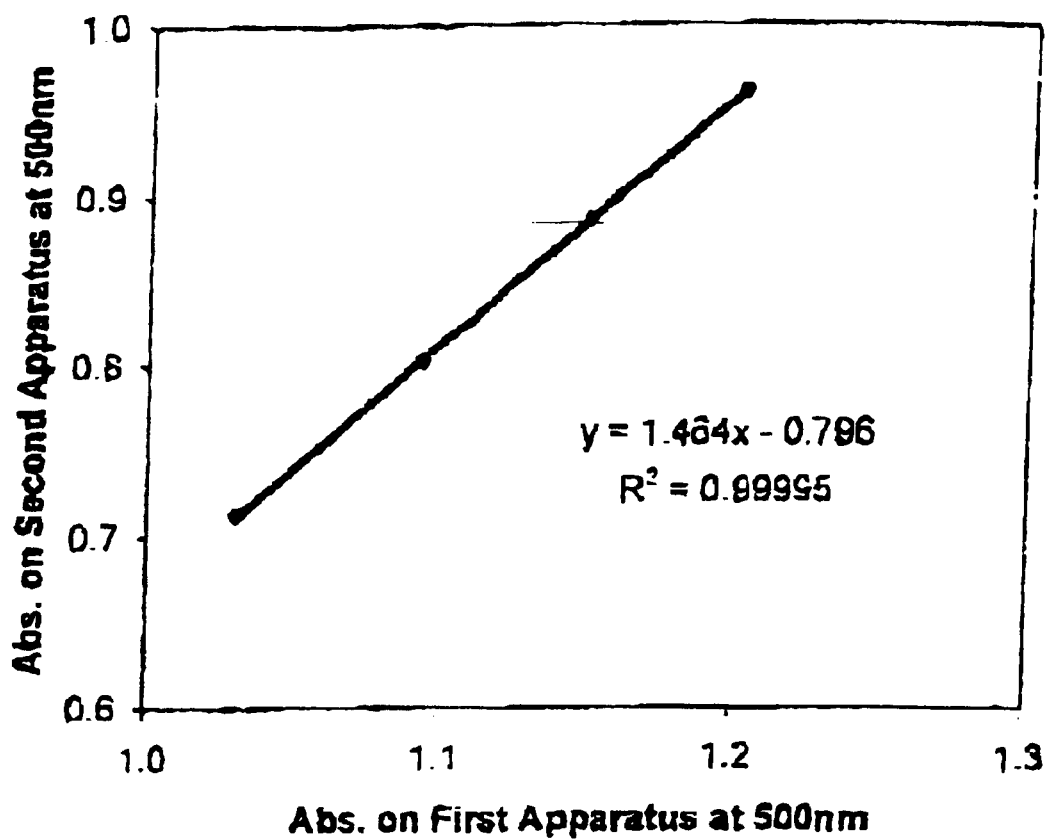
FIG. 3 is scatter plot of the absorbances of the four calibrators at 500 nm, when tested on the First Apparatus (x-axis) and the Second Apparatus (y-axis)
Figure 4:
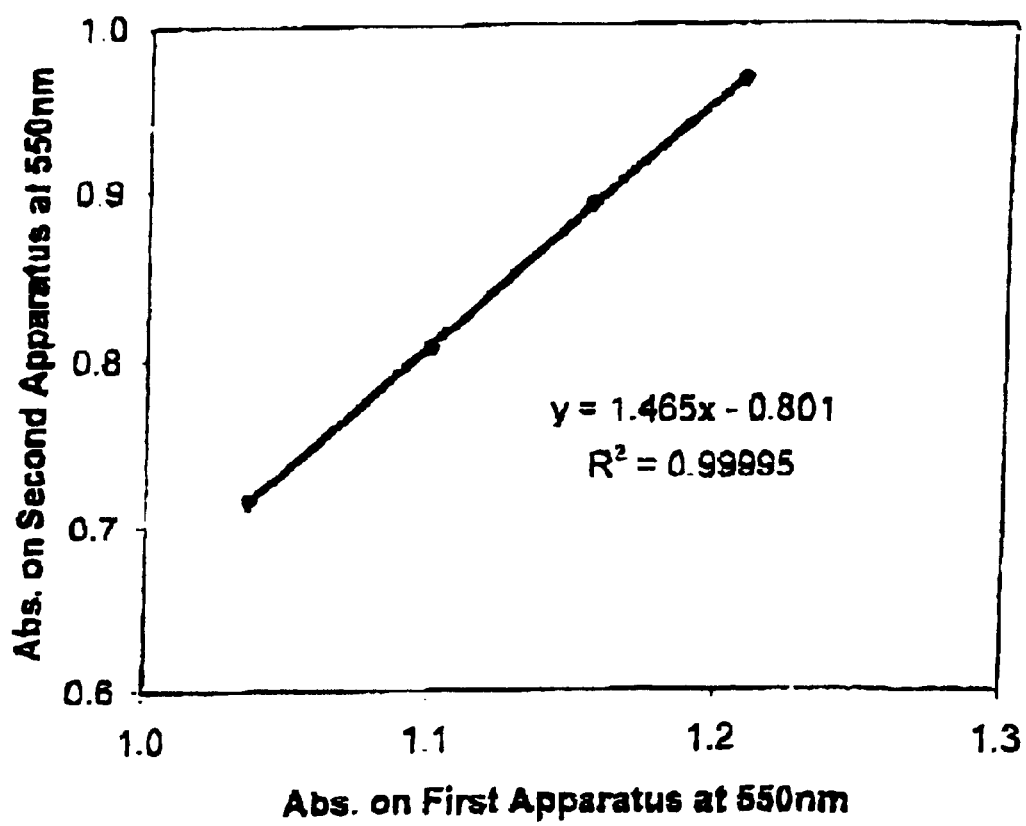
FIG. 4 is scatter plot of the absorbances of the four calibrators at 550 nm, when tested on the First Apparatus (x-axis) and the Second Apparatus (y-axis)
Figure 5:
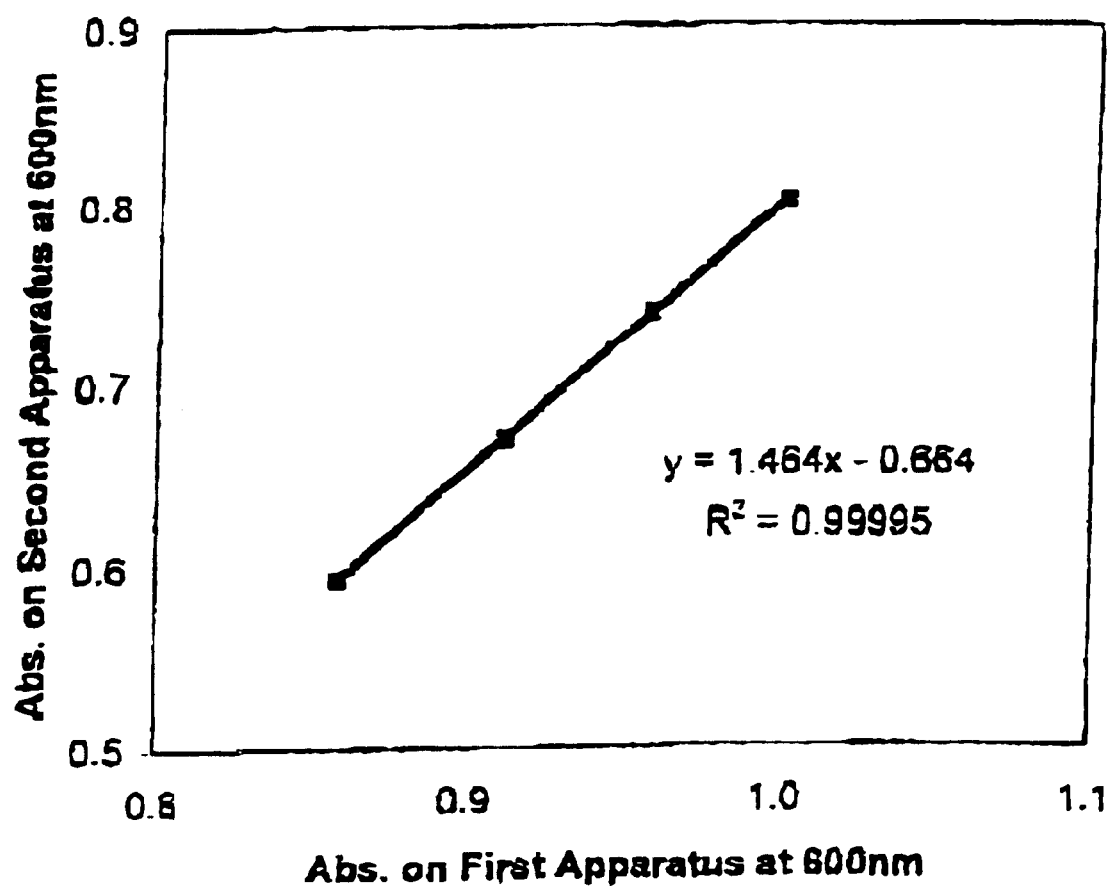
FIG. 5 is scatter plot of the absorbances of the four calibrators at 600 nm, when tested on the First Apparatus (x-axis) and the Second Apparatus (y-axis)
Figure 6:
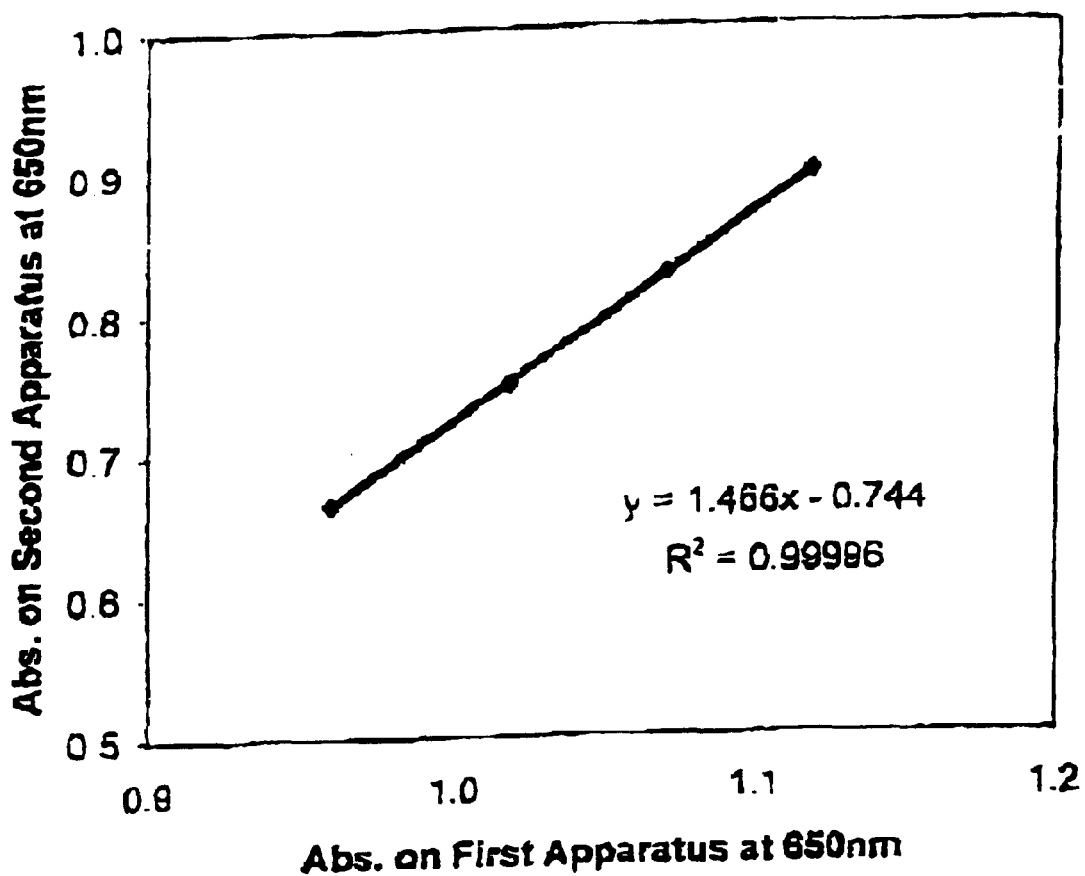
FIG. 6 is scatter plot of the absorbances of the four calibrators at 650 nm, when tested on the First Apparatus (x-axis) and the Second Apparatus (y-axis)
Figure 7:
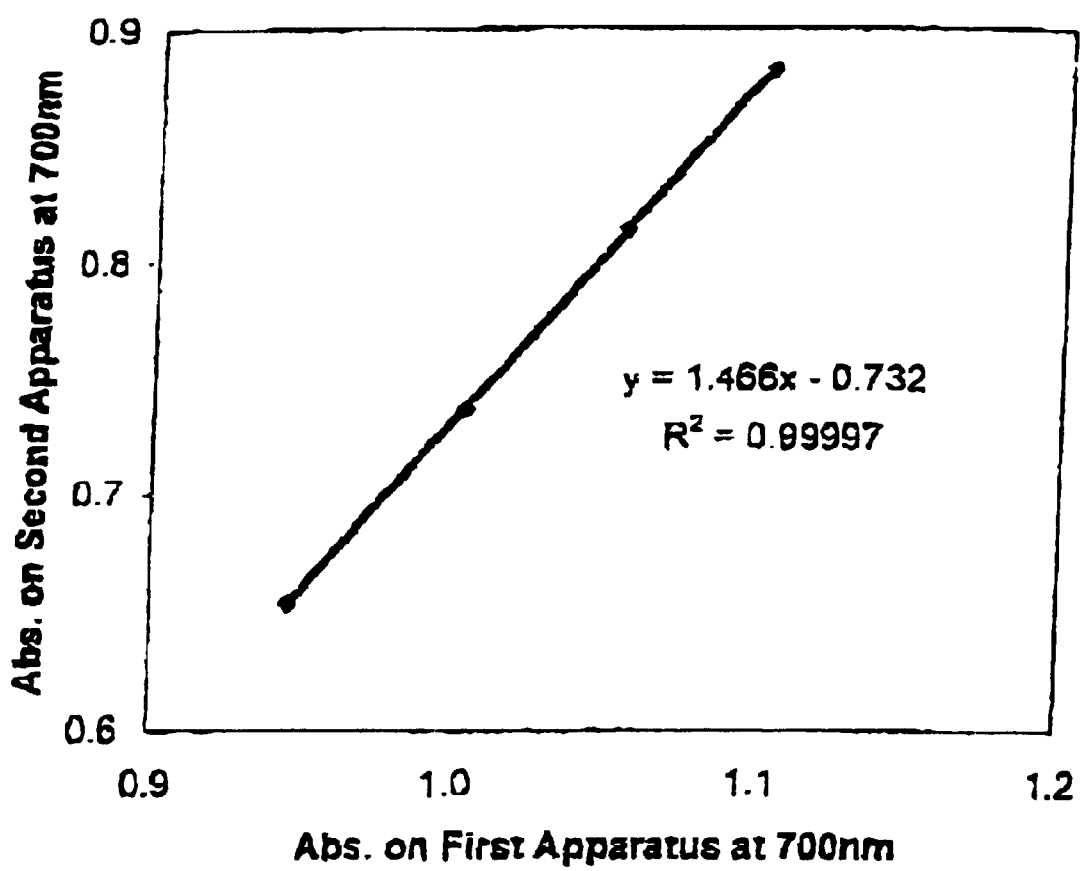
FIG. 7 is scatter plot of the absorbances of the four calibrators at 700 nm, when tested on the First Apparatus (x-axis) and the Second Apparatus (y-axis)
Figure 8:
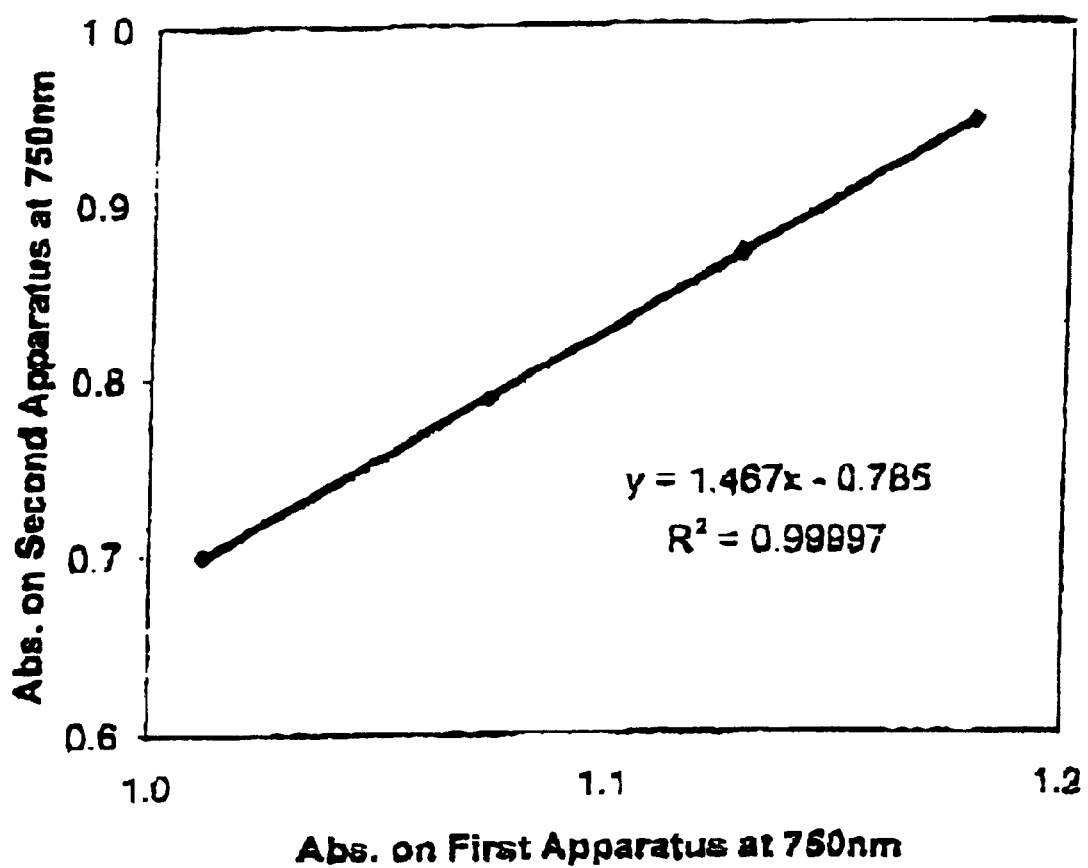
FIG. 8 is scatter plot of the absorbances of the four calibrators at 750 nm, when tested on the First Apparatus (x-axis) and the Second Apparatus (y-axis).

The absorbance spectra of four calibrators when tested on a first apparatus are shown in FIG. 1; the absorbance spectra obtained from a second apparatus are shown in FIG. 2. The first linear regression plots and equations for standard wavelengths 500 nm, 550 nm, 600 nm, 650 nm, 700 nm and 750 nm are shown in FIGS. 3, 4, 5, 6, 7, and 8 respectively. Table 1 shows the y-intercepts and slopes for the wavelengths chosen as examples.

TABLE 1

| Wavelength (nm) | y-intercept | Slope | $R^2$ |
|---|---|---|---|
| 500 | −0.796 | 1.464 | 0.99995 |
| 550 | −0.801 | 1.465 | 0.99995 |
| 600 | −0.664 | 1.464 | 0.99995 |
| 650 | −0.744 | 1.466 | 0.99996 |
| 700 | −0.732 | 1.466 | 0.99997 |
| 750 | −0.785 | 1.467 | 0.99997 |

The slopes are very similar for the wavelength example shown in Table 1, but there are more significant differences for the y-intercepts. These numbers are very different from apparatus to apparatus. The large $R^2$ values (very close to 1) indicates the high correlation between the absorbances of the two apparatuses, and hence the reliability of the photometric corrections.

The y-intercepts and slopes in Table 1 were derived from the first linear regression Plots of absorbances for the calibrators obtained on the first apparatus (x-axis) and second apparatus (y-axis).

The equation for wavelength 600 nm is y=1.464x−0.664, or in a more general form.

$$\text{Absorbance}_{Second} = 1.464 \times \text{Absorbance}_{First} - 0.664$$

Let us say that the absorbance for a particular sample at 600 nm on a Second Apparatus was 1.500. Before the calibration algorithm from the first apparatus (primary calibration algorithm) for any analyte can be applied to the absorbances measured on second apparatus, the following adjustments must be made:

$$\text{Adjusted absorbance} = (\text{Measured absorbance} - \{-0.664\})/1.464$$
$$= (\text{Measured absorbance} + 0.664)/1.464$$
$$= (1.500 + 0.664)/1.464$$
$$= 1.478$$

Where −0.664 is a y-intercept and 1.464 is the slope from table above, for 600 nm. All wavelengths involved in the calibration algorithms must be adjusted similarly.

Quality control must be tested before and after calibrators are tested on the first apparatus when preparing a calibration package, for assurance that the first apparatus is performing precisely as it was when the calibrator algorithms were developed. In order for a second apparatus to use the primary calibration algorithms derived for a first apparatus, preferably the following two items are required:
1). A table like Table 1 which includes at least the wavelengths used in the primary calibration algorithm(s), although all wavelengths may be incorporated;
2). A calibration set.

Example 2

For illustration, a primary Hb calibration algorithm was developed for apparatus #1, (a "First Apparatus"), and the same calibration algorithm was applied to data generated from five other apparatuses (#2, #3, #4, #5 and #6, all of which are second apparatus). In this example, calibration between instruments is illustrated using the first derivative of the absorbance spectra.

The absorbance spectra for the same sample was shown for only three of the apparatus for clarity (#2, #4 and #6); they demonstrated the full range of variability in the absorbance spectra for a standard set of wavelengths for the six apparatus used, without photometric correction (FIG. 9). When the first derivative of absorbance was calculated and plotted (FIG. 10), most of the variability disappeared, especially at wavelengths 593 nm and 608 nm, which were used in the calibration algorithm for hemoglobin, shown below:

g/L Hb=−0.22−75.96×(1st derivative of absorbance at 593 nm)+ 81.45×(1st derivative of absorbance at 608 nm)

FIG. 10 is a graphic representation of the first derivative of absorbance spectra of the same synthetic fluid tested on 3 different apparatus (#2, #4, #6) using a standard set of wavelengths. The wavelengths identified as 593 nm and 608 nm were used in the calibration algorithm for hemoglobin. A third wavelength, 537 nm, is shown to illustrate an area with significant differences in both the absorbances and first derivatives of absorbance.

Scatter plots of the predicted hemoglobin on instrument #1 (x-axis) vs the five other instruments (y-axis) are shown in FIGS. 11 to 15.

Figure 11:
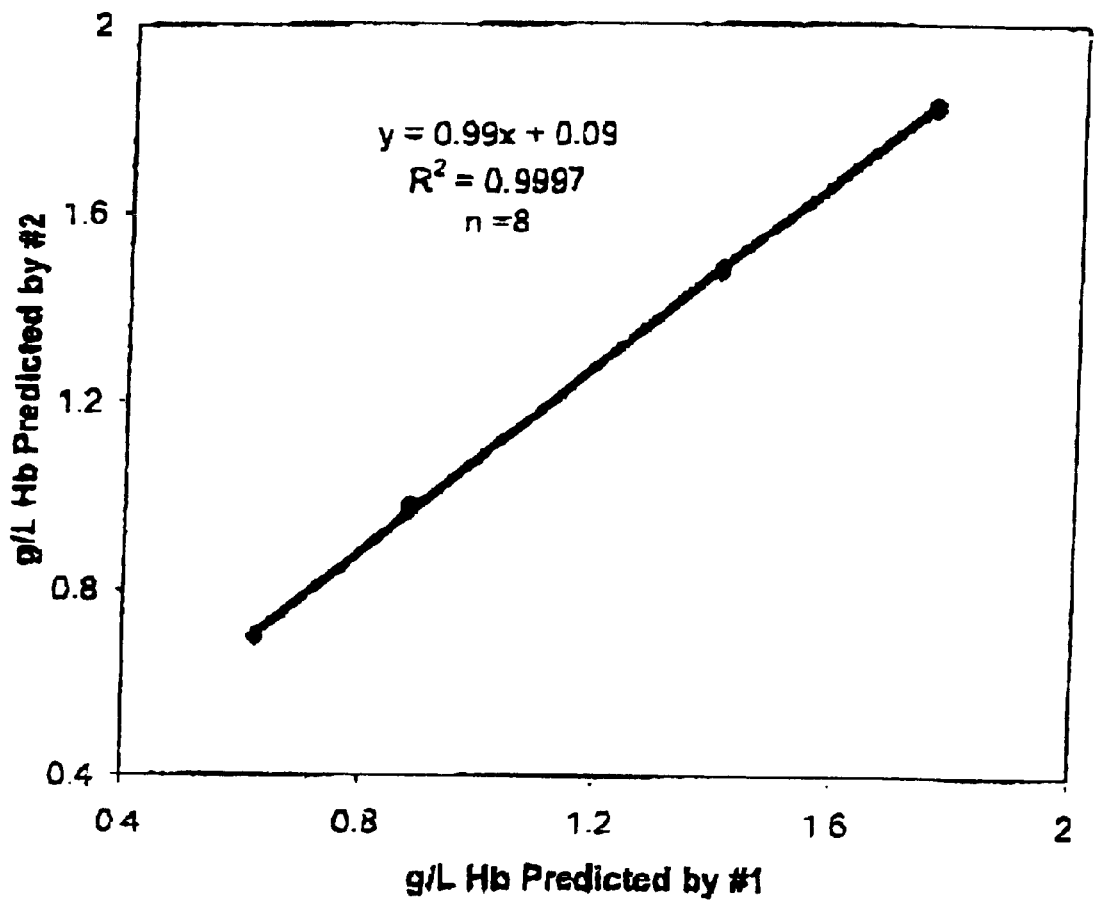
FIG. 11 is a scatter plot of the predicted Hb using the calibration algorithm of Example 2 in g/L.

FIG. 11 is a scatter plot of the predicted Hb in g/L using the same calibration equation {g/L Hb=−0.22−75.96×(1st derivative of absorbance at 593 nm)+81.45×(1st derivative of absorbance at 608 nm)} applied to data collected from instrument #1 (x-axis) and instrument #2 (y-axis)

Figure 12:
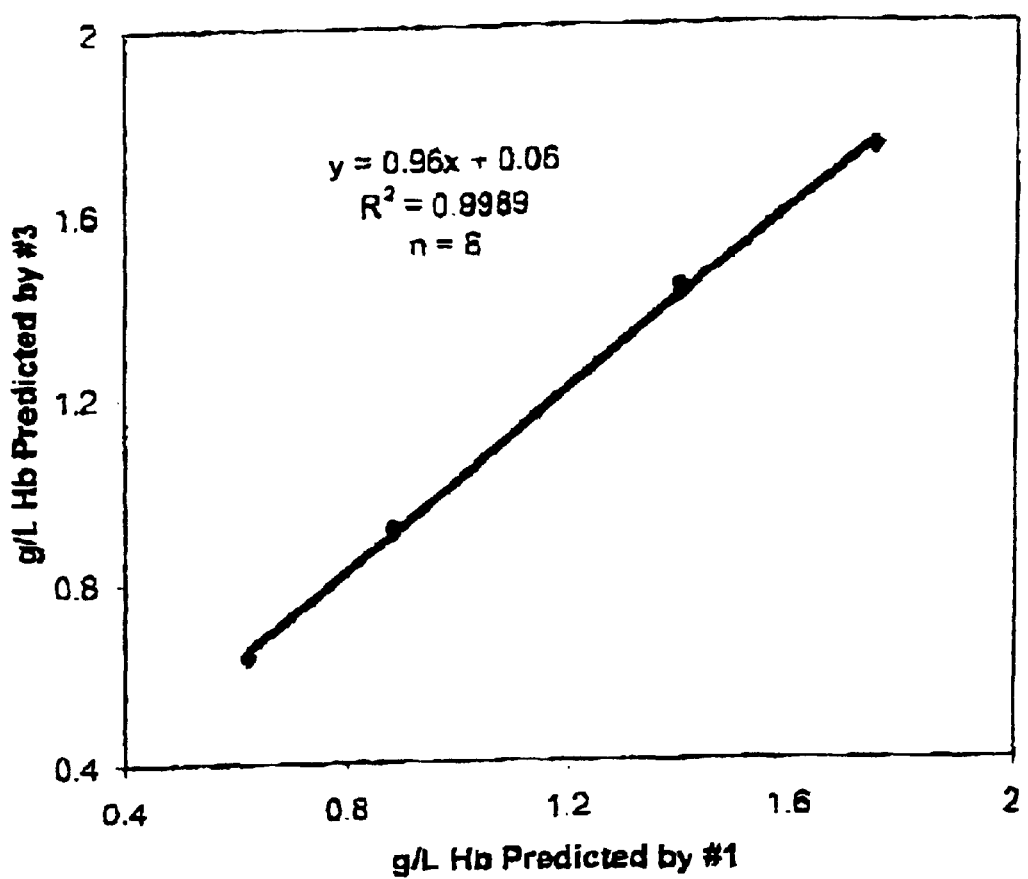
FIG. 12 is a scatter plot of the predicted Hb in g/L Hb using the calibration algorithm of Example 2.

FIG. 12 is a scatter plot of the predicted Hb in g/L using the same calibration equation {g/L Hb=−0.22−75.96×(1st derivative of absorbance at 593 nm)+81.45×(1st derivative of absorbance at 608 nm)} applied to data collected from instrument #1 (x-axis) and instrument #3 (y-axis)

Figure 13:
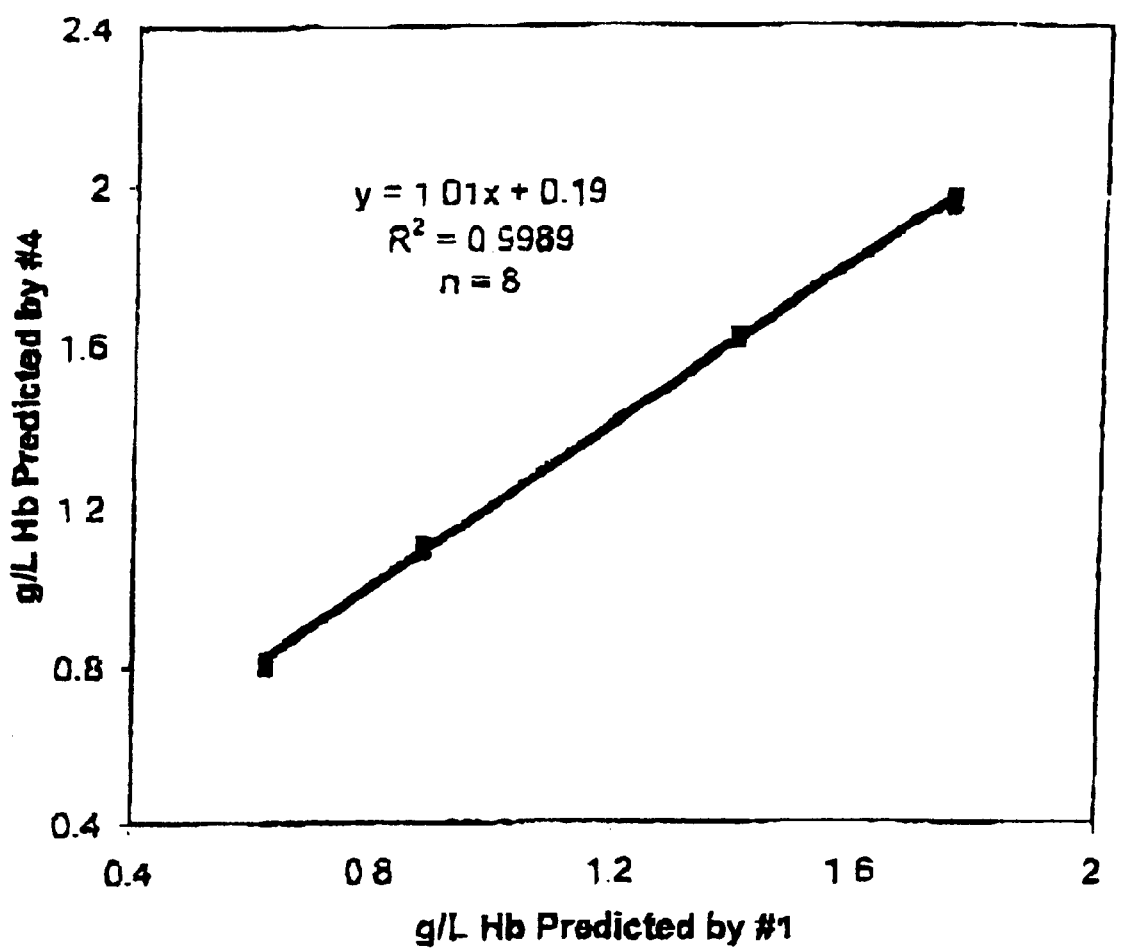
FIG. 13 is a scatter plot of the predicted Hb in g/L Hb using the calibration algorithm of Example 2.

FIG. 13 is a scatter plot of the predicted Hb in g/L using the same calibration equation {g/L Hb=−0.22−75.96×(1st derivative of absorbance at 593 nm)+81.45×(1st derivative of absorbance at 608 nm)} applied to data collected from instrument #1 (x-axis) and instrument #4 (y-axis)

Figure 14:
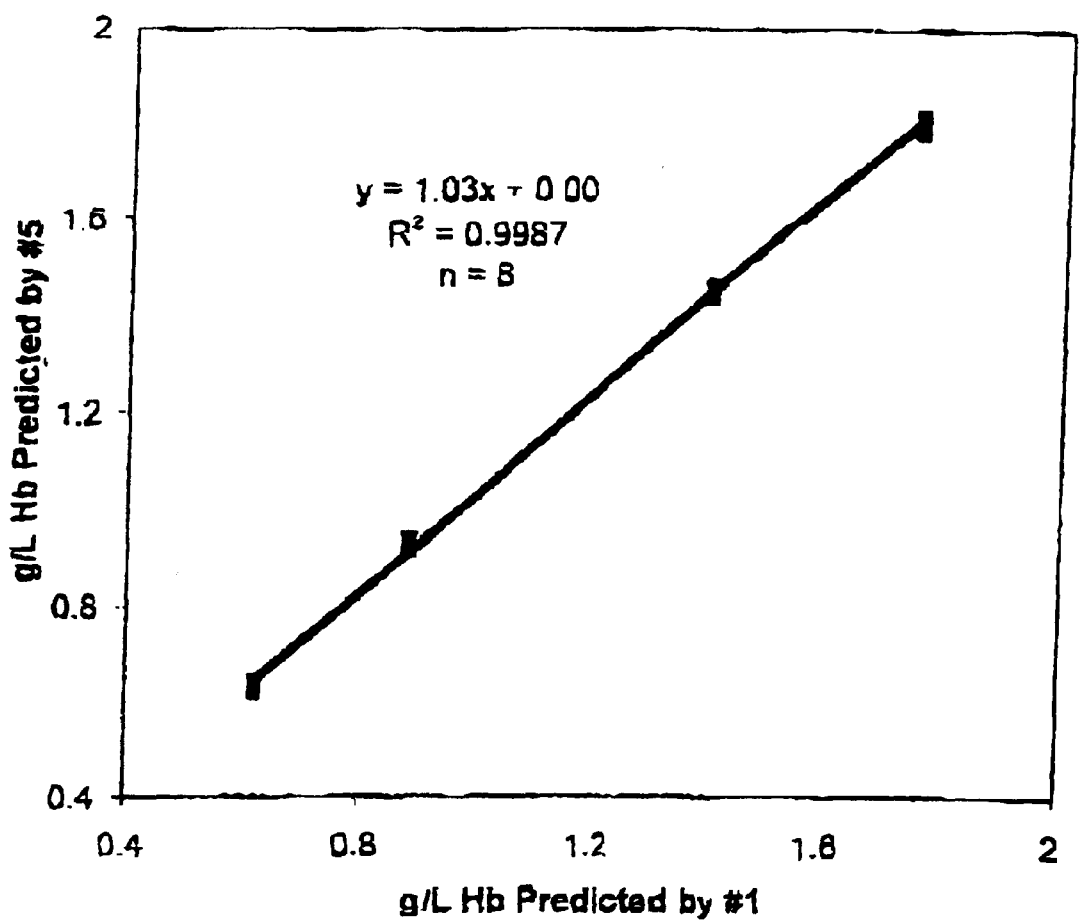
FIG. 14 is a scatter plot of the predicted Hb in g/L Hb using the calibration algorithm of Example 2.

FIG. 14 is a scatter plot of the predicted Hb in g/L using the same calibration equation {g/L Hb=−0.22−75.96×(1st derivative of absorbance at 593 nm)+81.45×(1st derivative of absorbance at 608 nm)} applied to data collected from instrument #1 (x-axis) and instrument #5 (y-axis)

Figure 15:
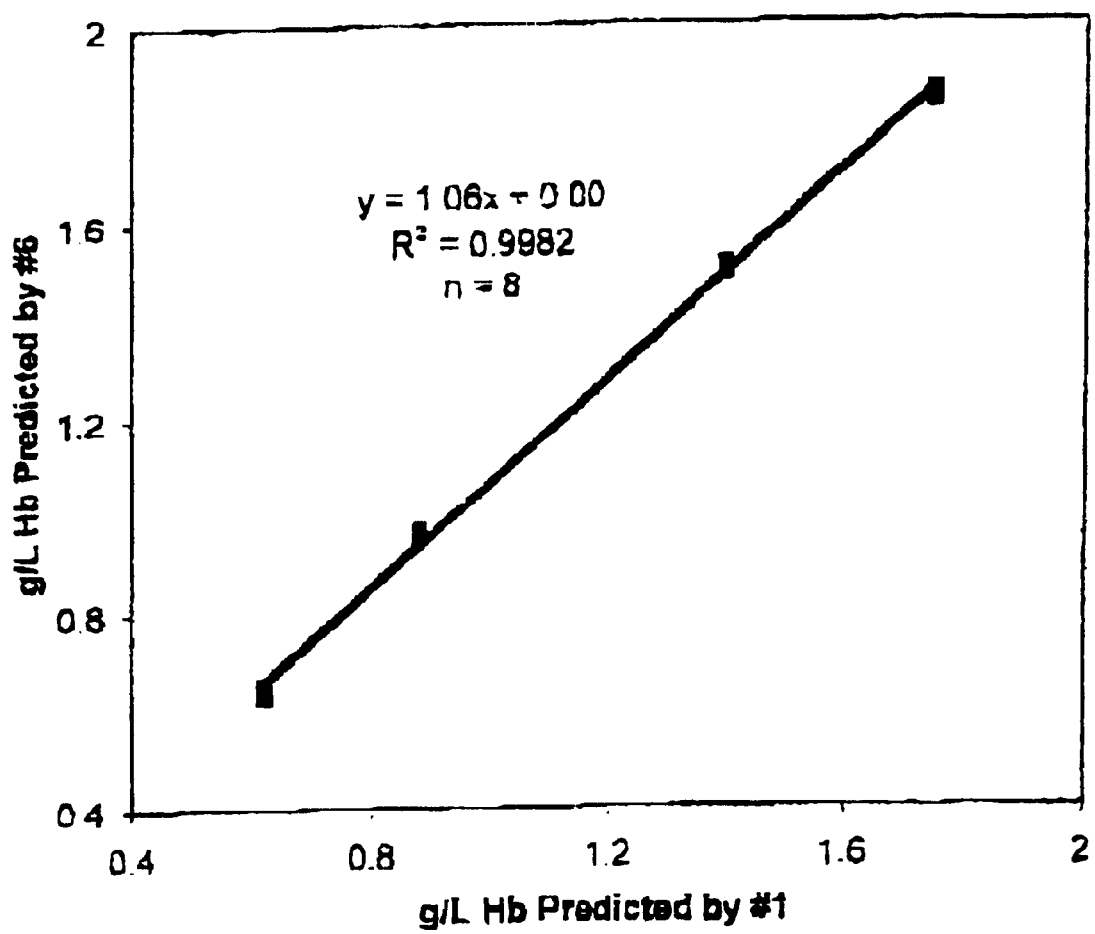
FIG. 15 is a scatter plot of the predicted Hb in g/L Hb using the calibration algorithm of Example 2.

FIG. 15 is a scatter plot of the predicted Hb in g/L using the same calibration equation {g/L Hb=−0.22−75.96×(1st derivative of absorbance at 593 nm)+81.45×(1st derivative of absorbance at 608 nm)} applied to data collected from instrument #1 (x-axis) and instrument #6 (y-axis)

These data clearly demonstrate that for the calibration algorithm of Hb set out in this example, no photometric correction was necessary because the two wavelengths chosen, demonstrated very little variability in the first derivative of absorbance that was used in the calibration algorithm.

Example 3

Upon examination of the spectra in FIG. 9, it may be seen that photometric correction would be necessary if the raw absorbances at any wavelength were used in the calibration algorithm. Upon examination of the first derivative of absorbance spectra of the same synthetic fluid tested on the same 3 different apparatus (#2, #4, #6) in FIG. 9, it is observed that there are no differences in the apparatus at 593 nm and 608 nm, using a standard set of wavelengths. It can be appreciated by those skilled in the art that the requirement of photometric correction depends on the required accuracy of the predicted analyte.

Example 4

Upon examination of the spectra in FIG. 10, it is observed that photometric correction would be necessary if the first derivative of absorbance at a wavelength like 537 nm was a major component in the primary calibration algorithm. It is also obvious that the requirement of photometric correction depends on the required prediction accuracy of the analyte, and the number of wavelengths like 593 nm used in the calibration algorithm. If PLS analysis or PCA, which use the full spectrum or continuous segments of the spectrum (raw absorbance or an order of derivative of absorbance) is used, there may be a greater need to perform photometric correction.

Example 5

FIG. 16 is a graphic representation of the second derivative of absorbance spectra of the same synthetic fluid tested on 3 different apparatuses (#2, #4, #6) using a standard set of wavelengths. The wavelengths identified as 593 nm and 608 nm were used in the calibration algorithm for hemoglobin when the first derivative of absorbance was used. For the purpose of calibration algorithm transfer one can visually observe the variability in the second derivative of absorbance; if the second derivative of absorbance was used to generate a calibration algorithm for hemoglobin, it seems obvious that 630 nm (shown) would be preferred to 593 nm. It should be noted that the best wavelength(s) used for calibration algorithm transfer (i.e., minimize inter-apparatus variability in predicted analyte concentration) are not necessarily the best wavelength(s) that produce(s) accurate hemoglobin predictions.

It is very clear from FIG. 9 (Absorbance) and FIG. 10 that the first derivative of absorbance removes most of the spectral variability between the three apparatuses. However, as higher derivatives are used, the number of peaks in the spectrum increases, and therefore the peaks become sharper. To illustrate, compare the number of peaks and their sharpness in FIG. 16 (second derivative absorbance) with FIG. 15 (first derivative absorbance). This is seen even more so in the third derivative (FIG. 19). Beyond the second derivative, the number of peaks do not change, but they become progressively sharper.

Example 6

Figure 17:
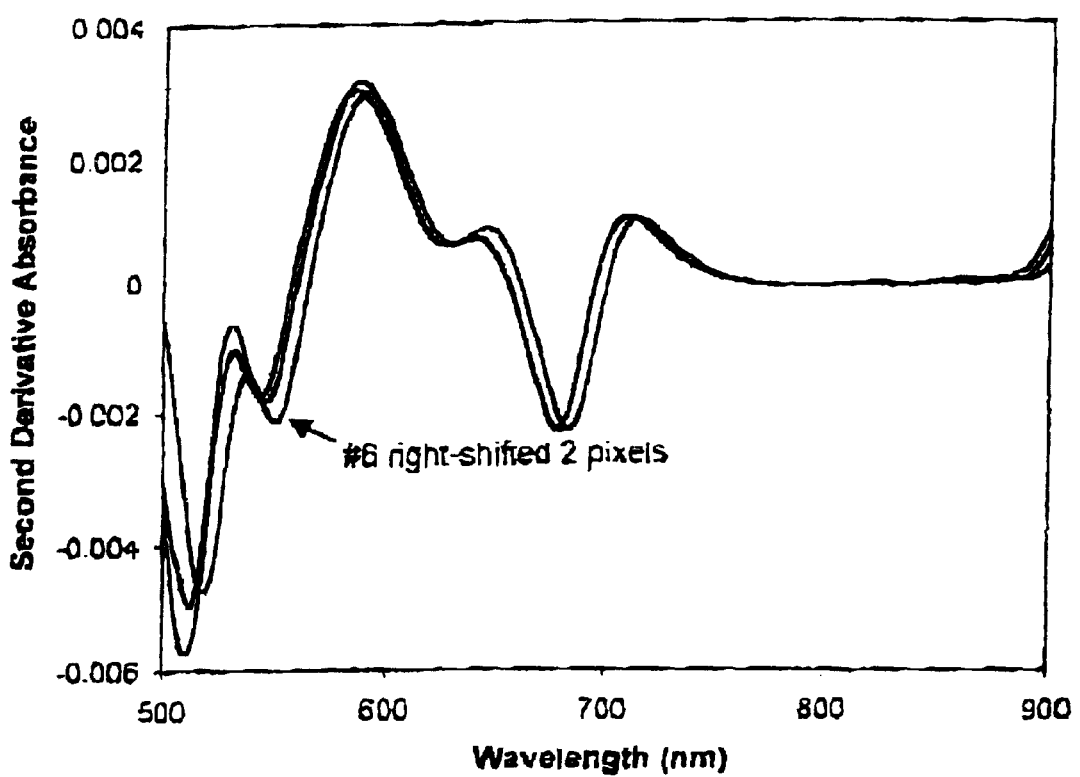
FIG. 17 is a graphic representation of the second derivative of absorbance spectra of the same synthetic fluid tested on 3 different apparatuses using a standard set of wavelength, and shifting the second derivative of absorbances for apparatus #6 to the right by 2 pixels.
Figure 18:
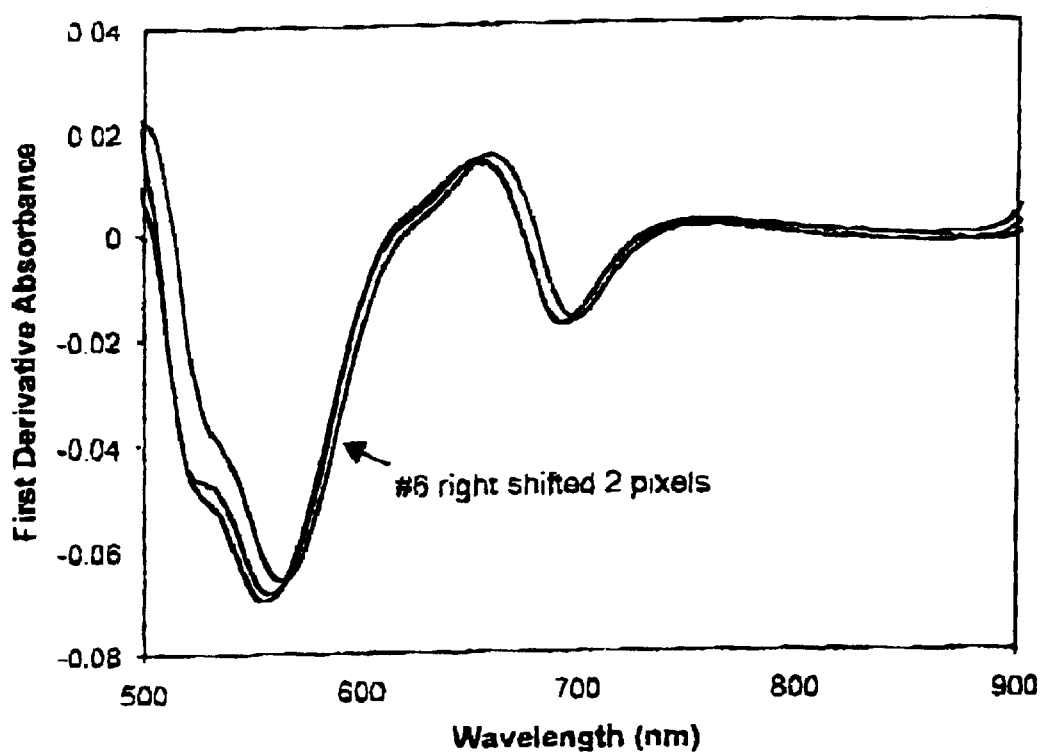
FIG. 18 is a graphic representation of the first derivative of absorbance spectra of the same synthetic fluid tested on 3 different apparatuses (#2, #4, #6) using a standard set of wavelength, and shifting the first derivative of absorbances for apparatus #6 to the right by 2 pixels.

A manufacturer calibrates spectrophotometers by using a single laser projected on the same pixel of each linear diode array detector, and uses a predetermined pixeldispersion. Therefore the apparatus using these spectrophotometers all have the same wavelength calibration table. Assume that three such apparatus are #2, #4, and #6 used to generate the absorbance spectra shown in FIG. 9. Furthermore, assume that there is an error in the wavelength calibration of apparatus # 6. In order to simulate this error, the absorbances of the sample tested on apparatus #6, are shifted by 2 pixels. FIG. 17 is a graphic representation of the second derivative of absorbance spectra of the same sample tested on 3 different apparatuses using a standard set of wavelength, and shifting the second derivative of absorbances for apparatus #6 to the right by 2 pixels. FIG. 18 is a graphic representation of the first derivative of absorbance spectra of the same sample tested on 3 different apparatuses (#2, #4, #6) using a standard set of wavelength, and shifting the first derivative of absorbances for apparatus #6 to the right by 2 pixels. Although the derivative of absorbance may remove some of the variability in absorbance as explained in Example 2, the impact of wavelength inaccuracy on the derivative of absorbance is demonstrated in FIG. 17 and FIG. 18, for the second derivative of absorbance and first derivative of absorbance respectively. This example demonstrates the importance of wavelength accuracy between apparatus. The magnitude of the wavelength error that is acceptable depends on the required accuracy of the analyte measurement. A preferred method to deal with wavelength inaccuracy is to use two wavelengths for wavelength calibration, whereby the pixel dispersion can be calculated for each apparatus; generate a wavelength calibration table for each apparatus, and map the measured absorbances to a standard set of wavelengths. It is also preferred that subsequent to the mapping of absorbances, that a Calibration Set be used to perform photometric correction for the relevant wavelengths.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

The above description is not intended to limit the claimed invention in any manner, furthermore, the discussed combination of features might not be absolutely necessary for the inventive solution.

All publications, patents and patent applications referred to herein are incorporated by reference in their entirety to the same extent as if each individual publication, patent or patent application was specifically and individually indicated to be incorporated by reference in its entirety.

I claim:

1. A method of determining the concentration of one or more Analytes in a Sample in a second apparatus comprising:
   (i) providing the second apparatus having at least one primary calibration algorithm for each of the one or more analytes, as obtained from one or more than one first apparatus, the at least one primary calibration algorithm using an order derivative of absorbance obtained for at least one of a standard set of wavelengths, wherein wavelengths of the standard set of wavelengths are the same as, or different from, wavelengths of a wavelength calibration table for the first apparatus, the second apparatus, or both the first and the second apparatus;
   (ii) measuring absorbance values of the sample at one or more than one wavelength from the standard set of wavelengths on the second apparatus;
   (iii) calculating a concentration of the one ore more Analyte in the sample, by applying the at least one Primary Calibration Algorithm to the order derivative of the absorbance values.

2. The method according to claim 1, wherein in the step of providing (step (i)), and in the step of calculating (step (iii)), the order derivative, is selected from the group consisting of a zero order derivative, a first order derivative, a second order derivative, and a third order derivative.

3. The method according to claim 1, wherein a statistical technique selected from the group consisting of simple linear regression, multiple linear regression, and Multivariate data analysis, is used to process absorbance measurements for the development of the at least one primary calibration algorithm.

4. The method according to claim 3, wherein the Multivariate data analysis is selected from the group consisting of Principal Component Analysis, Principal Component Regression, Partial Least Squares regression, and Neural Network.

5. The method of claim 1 wherein data pre-processing follows the step of measuring (step (ii)).

6. The method according to claim 5, wherein data pre-processing is selected from the group consisting of calculation of interpolated absorbances; smoothing of absorbances; calculation of a first and higher order derivative of absorbance; multiplicative scatter correction; data transformation; photometric correction, and any combination thereof.

7. The method of claim 1 wherein the second apparatus comprises a second linear diode array comprising the same number of pixels as a first linear diode array in a first apparatus.

8. The method of claim 1, wherein in the step of providing (step (i)), and wherein in the step of measuring (step (ii)), the standard set of wavelengths is a set of approximate wavelengths derived from a wavelength calibration table of one, or more than one, first apparatus, one, or more than one, of the second apparatus, or both the one, or more than one, first and the one, or more than one of the second apparatus.

9. The method according to claim 1, wherein in the step of providing (step (i)), and wherein in the step of measuring (step (ii)), the standard set of wavelengths comprises wavelengths that are common to a wavelength calibration table of both a first apparatus used to obtain the primary calibration algorithm, and the second apparatus.

10. The method of claim 1, wherein the standard set of wavelengths comprises wavelengths from about 300 nm to about 2500 nm.

11. The method of claim 1, wherein the standard set of wavelengths comprises wavelengths from about 500 nm to about 1100 nm.

12. The method according to claim 1, wherein the sample is placed in a like vessel having optical properties substantially similar to that used for the primary calibration.

13. The method according to claim 12, wherein the vessel is selected from the group consisting of a pipette tip, a labeled test tube, an unlabeled test tube, blood bag tubing, a transparent sample container, and a translucent sample container.

14. The method according to claim 1, wherein the sample is any biological or non-biological fluid, and the analyte is any substance in the sample for which an absorbance measurement can be obtained.

15. The method according to claim 1, wherein the sample is a solid, and the analyte is any substance in the sample for which an absorbance measurement can be obtained.

16. The method according to claim 15, wherein the sample is any body part.

17. The method according to claim 1, wherein in the steps of providing (step (i)), and measuring (step (ii)), the standard set of wavelengths is obtained by creating a table of approximate wavelengths derived from one or more first, one or more second, or both the one or more first and the one or more second, wavelength calibration tables, wherein a pixel number of a linear diode array of the first apparatus and a pixel number of a second linear diode array of the second apparatus must be within less than or equal to about ±N pixels of a reference pixel number of the first apparatus, where, N is a number of pixels that encompass a range of wavelengths of no more than about ±20 nm, wherein the reference pixel number of the first apparatus is associated with a known wavelength of electromagnetic radiation.

18. The method of claim 1, wherein the wavelength calibration table for the first apparatus or the second apparatus is obtained by:
   (i) projecting a first electromagnetic radiation of known wavelength, onto a first pixel of a first linear diode array of the first apparatus, or a second linear diode array of the second apparatus;
   (ii) using a second electromagnetic radiation of known wavelength, the second electromagnetic radiation having a different wavelength than the first electromagnetic radiation, projecting the second electromagnetic radiation onto a second pixel of the first or the second linear diode array;
   (iii) identifying the first and second pixels within the first or the second linear diode array;
   (iv) calculating a pixeldispersion for the first or the second linear diode array; and
   (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

19. The method according to claim 17, wherein the range of wavelengths is about ±20 nm.

20. The method according to claim 17, wherein the range of wavelengths is about ±10 nm.

21. The method according to claim 17, wherein the range of wavelengths is about ±5 nm.

22. The method according to claim 17, wherein the range of wavelengths is about ±2 nm.

23. The method according to claim 1, wherein the wavelength calibration table for the first or the second apparatus is obtained by:
   (a) projecting a known wavelength of electromagnetic radiation, onto a pixel in a linear diode array of the first apparatus, or the second apparatus;
   (b) identifying pixel number of the pixel;
   (c) assigning a wavelength to each pixel within the linear diode array to produce the first, second, or both the first and the second wavelength calibration table using a predetermined pixeldispersion, the known wavelength of electromagnetic radiation and the pixel number.

24. The method according to claim 1, wherein the step of measuring (step(ii)) further comprises:
   (A) obtaining absorbance of the sample on the second apparatus, at two or more than two wavelengths from a first wavelength calibration table that encompass one or more than one wavelengths of a standard set of wavelengths;
   (B) determining an interpolated absorbance of the sample for one or more than one wavelength of the standard set of wavelengths; and
   the step of calculating (step iii)) comprises: replacing the absorbance measurements with the interpolated absorbance determined in step (B).

25. The method according to claim 24, wherein the interpolated absorbance is adjusted, to produce an adjusted interpolated absorbance determined by:
   (a) establishing a first set of absorbance measurements of a set of calibrators on one or more than one First Apparatus for one or more than one wavelength from the first wavelength calibration table;
   (b) obtaining a second set of absorbance measurements of the same set of calibrators or a similar set of calibrators on the Second Apparatus, for one or more than one wavelength from the second wavelength calibration table;
   (c) determining a first interpolated absorbance for the first set of absorbance measurements for one or more than one wavelength of a standard set of wavelengths, and determining a second interpolated absorbance for the second set of absorbance measurements for the one or more than one wavelength of the standard set of wavelengths, (d) deriving a linear regression equation for one or more than one wavelength of the standard set of wavelengths using the first and the second set of interpolated absorbance measurements; and (e) using the linear regression equation to obtain the adjusted interpolated absorbance, wherein in the step of using (step (e)), the adjusted interpolated absorbance (AIA) is obtained from the following equation:

AIA=(interpolated absorbance−y-intercept)/slope;

wherein, "y-intercept" and "slope" are obtained from the linear regression equation, where the linear regression equation is derived from a plot of interpolated absorbance measurements, the first interpolated absorbance measurements on an X-axis, and the second interpolated absorbance measurements on a Y-axis, the linear regression equation having a y-intercept and a slope.

26. The method according to claim 25, wherein in the step of providing (step (i)), and in the step of calculating (step (iii)), the order derivative, is selected from the group consisting of a zero order derivative, a first order derivative, a second order derivative, and a third order derivative.

27. The method according to claim 25, wherein a statistical technique selected from the group consisting of simple linear regression, multiple linear regression, and Multivariate data analysis, is used to process absorbance measurements for the development of the at least one primary calibration algorithm.

28. The method according to claim 27, wherein the Multivariate data analysis is selected from the group consisting of Principal Component Analysis, Principal Component Regression, Partial Least Squares regression, and Neural Network.

29. The method of claim 25, wherein the second apparatus comprises a second linear diode array comprising the same number of pixels as a first linear diode array in a first apparatus.

30. The method of claim 25, wherein the standard set of wavelengths comprises wavelengths from about 300 nm to about 2500 nm.

31. The method of claim 25, wherein the standard set of wavelengths comprises wavelengths from about 500 nm to about 1100 nm.

32. The method according to claim 25, wherein the sample is placed in a like vessel having optical properties substantially similar to that used for the primary calibration.

33. The method according to claim 32, wherein the vessel is selected from the group consisting of a pipette tip, a labeled test tube, an unlabeled test tube, blood bag tubing, a transparent sample container, and a translucent sample container.

34. The method according to claim 25, wherein the sample is any biological or non-biological fluid, and the analyte is any substance in the sample for which an absorbance measurement can be obtained.

35. The method according to claim 25, wherein the sample is a solid, and the analyte is any substance in the sample for which an absorbance measurement can be obtained.

36. The method according to claim 25, wherein the sample is any body part.

37. The method according to claim 25, wherein the wavelength calibration table for the first apparatus or the second apparatus is obtained by:

(i) projecting a first electromagnetic radiation of known wavelength, onto a first pixel of a first linear diode array of the first apparatus, or a second linear diode array of the second apparatus;

(ii) using a second electromagnetic radiation of known wavelength, the second electromagnetic radiation having a different wavelength than the first electromagnetic radiation, projecting the second electromagnetic radiation onto a second pixel of the first or the second linear diode array;

(iii) identifying the first and second pixels within the first or the second linear diode array;

(iv) calculating a pixeldispersion for the first or the second linear diode array; and (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

38. The method according to claim 25, wherein the wavelength calibration table for the first or the second apparatus is obtained by:

(a) projecting a known wavelength of electromagnetic radiation, onto a pixel in a linear diode array of the first apparatus, or the second apparatus;

(b) identifying pixel number of the pixel;

(c) assigning a wavelength to each pixel within the linear diode array to produce the first, second, or both the first and the second wavelength calibration table using a predetermined pixeldispersion, the known wavelength of electromagnetic radiation and the pixel number.

39. The method according to claim 25, wherein in the step of deriving (step (d)), two or more calibrators are used.

40. The method according to claim 39, wherein the calibrators comprise any material suitable for simulating absorbances and for producing at least one of the First Linear Regression Equation.

41. The method according to claim 25, wherein in the step of establishing (step (a)), the first set of absorbance measurements, in the step of obtaining (step (b)), the second set of absorbance measurements, or both the first and the second set of absorbance measurements, are determined one or more times at each wavelength of a wavelength calibration table, and either:

an average of the first interpolated absorbance or the second interpolated absorbance value is used, or averages of the first set of absorbance measurements, or averages of the second set of absorbance measurements are interpolated and mapped to the standard set of wavelengths.

42. The method according to claim 24, wherein in the step of providing (step (i)), and in the step of calculating (step (iii)), the order derivative, is selected from the group consisting of a zero order derivative, a first order derivative, a second order derivative, and a third order derivative.

43. The method according to claim 24, wherein a statistical technique selected from the group consisting of simple linear regression, multiple linear regression, and Multivariate data analysis, is used to process absorbance measurements for the development of the at least one primary calibration algorithm.

44. The method according to claim 43, wherein the Multivariate data analysis is selected from the group consisting of Principal Component Analysis, Principal Component Regression, Partial Least Squares regression, and Neural Network.

45. The method of claim 24, wherein the second apparatus comprises a second linear diode array comprising the same number of pixels as a first linear diode array in a first apparatus.

46. The method of claim 24, wherein the standard set of wavelengths comprises wavelengths from about 300 nm to about 2500 nm.

47. The method of claim 24, wherein the standard set of wavelengths comprises wavelengths from about 500 nm to about 1100 nm.

48. The method according to claim 24, wherein the sample is placed in a like vessel having optical properties substantially similar to that used for the primary calibration.

49. The method according to claim 48, wherein the vessel is selected from the group consisting of a pipette tip, a labeled test tube, an unlabeled test tube, blood bag tubing, a transparent sample container, and a translucent sample container.

50. The method according to claim 24, wherein the sample is any biological or non-biological fluid, and the analyte is any substance in the sample for which an absorbance measurement can be obtained.

51. The method according to claim 24, wherein the sample is a solid, and the analyte is any substance in the sample for which an absorbance measurement can be obtained.

52. The method according to claim 24, wherein the sample is any body part.

53. The method according to claim 24, wherein the wavelength calibration table for the first apparatus or the second apparatus is obtained by:
  (i) projecting a first electromagnetic radiation of known wavelength, onto a first pixel of a first linear diode array of the first apparatus, or a second linear diode array of the second apparatus;
  (ii) using a second electromagnetic radiation of known wavelength, the second electromagnetic radiation having a different wavelength than the first electromagnetic radiation, projecting the second electromagnetic radiation onto a second pixel of the first or the second linear diode array;
  (iii) identifying the first and second pixels within the first or the second linear diode array;
  (iv) calculating a pixeldispersion for the first or the second linear diode array; and
  (v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

54. The method according to claim 24, wherein the wavelength calibration table for the first or the second apparatus is obtained by:
  (a) projecting a known wavelength of electromagnetic radiation, onto a pixel in a linear diode array of the first apparatus, or the second apparatus;
  (b) identifying pixel number of the pixel;
  (c) assigning a wavelength to each pixel within the linear diode array to produce the first, second, or both the first and the second wavelength calibration table using a predetermined pixeldispersion, the known wavelength of electromagnetic radiation and the pixel number.

55. The method according to claim 1, wherein in the step of calculating (step iii)), the concentration is reported in a qualitative manner.

56. The method according to claim 1, wherein in the step of providing (step (i)), the wavelengths of the standard set of wavelengths are different from the wavelengths of the wavelength calibration table on the second apparatus.

57. The method according to claim 1, wherein the at least one primary calibration algorithm is developed using combined absorbance data of samples measured on one or more than one apparatus.

58. The method of claim 57, wherein the combined absorbance data is subjected to data pre-processing prior to development of the primary calibration algorithm.

59. The method according to claim 58, wherein the data pre-processing is selected from the group consisting of calculation of interpolated absorbances; smoothing of absorbances; calculation of a first and higher order derivative of absorbance; multiplicative scatter correction; data transformation; photometric correction, and any combination thereof.

60. A method of determining the concentration of at least one Analyte in a Sample in a second apparatus comprising:
  (i) providing the second apparatus having at least one upgraded primary calibration algorithm for each of the one or more analytes, the at least one upgraded primary calibration algorithm developed by combining some, or all of an original primary calibration data set obtained from one or more first apparatus for at least one wavelength of a standard set of wavelengths, with additional data from the second apparatus, the additional data obtained using a smaller similar primary calibration set, a subset primary calibration set, or both, for at least one wavelength of a standard set of wavelengths, wherein the one or more wavelengths of the standard set of wavelengths are the same as, or different from, wavelengths of a wavelength calibration table for the first apparatus, the second apparatus, or both the first and the second apparatus;
  (ii) measuring absorbance values of the sample at one or more wavelengths from the standard set of wavelengths, on the second apparatus;
  (iii) calculating a concentration of the one or more Analyte in the sample, by applying the at least one Primary Calibration Algorithm to the order derivative of the absorbance measurements of step (ii).

61. The method according to claim 60, wherein in the step of providing (step (i)), and in the step of calculating (step (iii)), the order derivative, is selected from the group consisting of a zero order derivative, a first order derivative, a second order derivative, and a third order derivative.

62. The method according to claim 60, wherein a statistical technique selected from the group consisting of simple linear regression, multiple linear regression, and Multivariate data analysis, is used to process absorbance measurements for the development of the at least one primary calibration algorithm.

63. The method according to claim 62, wherein the Multivariate data analysis is selected from the group consisting of Principal Component Analysis, Principal Component Regression, Partial Least Squares regression, and Neural Network.

64. The method of claim 60, wherein data pre-processing follows the step of measuring (step (ii)).

65. The method according to claim 64, wherein data pre-processing is selected from the group consisting of calculation of interpolated absorbances; smoothing of absorbances; calculation of a first and higher order derivative of absorbance; multiplicative scatter correction; data transformation; photometric correction, and a combination any combination thereof.

66. The method of claim 60 wherein the second apparatus comprises a second linear diode array comprising the same number of pixels as a first linear diode array in a first apparatus.

67. The method of claim 60, wherein in the step of providing (step (i)), and wherein in the step of measuring (step (ii)), the standard set of wavelengths is a set of approximate wavelengths derived from a wavelength calibration table of one, or more than one, first apparatus, one, or more than one of the second apparatus, or both the one, or more than one first and the one, or more than one of the second apparatus.

68. The method according to claim 60, wherein in the step of providing (step (i)), and wherein in the step of measuring (step (ii)), the standard set of wavelengths comprises wavelengths that are common to a wavelength calibration table of both a first apparatus used to obtain the primary calibration algorithm, and the second apparatus.

69. The method of claim 60, wherein the standard set of wavelengths comprises wavelengths from about 300 nm to about 2500 nm.

70. The method of claim 60, wherein the standard set of wavelengths comprises wavelengths from about 500 nm to about 1100 nm.

71. The method according to claim 60, wherein the sample is placed in a like vessel having optical properties substantially similar to that used for the primary calibration.

72. The method according to claim 71, wherein the vessel is selected from the group consisting of a pipette tip, a labeled test tube, an unlabeled test tube, blood bag tubing, a transparent sample container, and a translucent sample container.

73. The method according to claim 60, wherein the sample is any biological or non-biological fluid, and the analyte is any substance in the sample for which an absorbance measurement can be obtained.

74. The method according to claim 60, wherein the sample is a solid, and the analyte is any substance in the sample for which an absorbance measurement can be obtained.

75. The method according to claim 60, wherein in the steps of providing (step (i)), and measuring (step (ii)), the standard set of wavelengths is obtained by creating a table of approximate wavelengths derived from one or more first, one or more second, or both the one or more first and the one or more second, wavelength calibration tables, wherein a pixel number of a linear diode array of the first apparatus and a pixel number of a second linear diode array of the second apparatus must be within less than or equal to about ±N pixels of a reference pixel number of the first apparatus, where, N is a number of pixels that encompass a range of wavelengths of no more than about ±20 nm, wherein the reference pixel number of the first apparatus is associated with a known wavelength of electromagnetic radiation.

76. The method according to claim 75, wherein the range of wavelengths is about ±20 nm.

77. The method according to claim 75, wherein the range of wavelengths is about ±10 nm.

78. The method according to claim 75, wherein the range of wavelengths is about ±5 nm.

79. The method according to claim 75, wherein the range of wavelengths is about ±2 nm.

80. The method according to claim 60, wherein the wavelength calibration table for the first apparatus or the second apparatus is obtained by:
(i) projecting a first electromagnetic radiation of known wavelength, onto a first pixel of a first linear diode array of the first apparatus, or a second linear diode array of the second apparatus;
(ii) using a second electromagnetic radiation of known wavelength, the second electromagnetic radiation having a different wavelength than the first electromagnetic radiation, projecting the second electromagnetic radiation onto a second pixel of the first or the second linear diode array;
(iii) identifying the first and second pixels within the first or the second linear diode array;
(iv) calculating a pixeldispersion for the first or the second linear diode array; and
(v) assigning a wavelength to each pixel within the first or the second linear diode array to produce the wavelength calibration table using the pixeldispersion and either the first electromagnetic radiation of known wavelength and the first pixel, or the second electromagnetic radiation of known wavelength and the second pixel.

81. The method according to claim 60, wherein the wavelength calibration table for the first or the second apparatus is obtained by:
(a) projecting a known wavelength of electromagnetic radiation, onto a pixel in a linear diode array of the first apparatus, or the second apparatus;
(b) identifying pixel number of the pixel;
(c) assigning a wavelength to each pixel within the linear diode array to produce the first, second, or both the first and the second wavelength calibration table using a predetermined pixeldispersion, the known wavelength of electromagnetic radiation and the pixel number.

82. The method according to claim 60, wherein the sample is any body part.

83. The method according to claim 60, wherein in the step of calculating (step iii)), the concentration is reported in a qualitative manner.

* * * * *